US010005081B2

(12) United States Patent
Duffy et al.

(10) Patent No.: US 10,005,081 B2
(45) Date of Patent: Jun. 26, 2018

(54) APPARATUS AND METHODS FOR ASPIRATING AND SEPARATING COMPONENTS OF DIFFERENT DENSITIES FROM A PHYSIOLOGICAL FLUID CONTAINING CELLS

(71) Applicant: EndoCellutions, Inc., Marshfield, MA (US)

(72) Inventors: Neil Francis Duffy, Brighton, MA (US); Jeffrey R. Chabot, Medford, MA (US)

(73) Assignee: EndoCellutions, Inc., Marshfield, MA (US)

( * ) Notice: Subject to any disclaimer, the term of this patent is extended or adjusted under 35 U.S.C. 154(b) by 63 days.

(21) Appl. No.: 15/041,588

(22) Filed: Feb. 11, 2016

(65) Prior Publication Data
US 2016/0263571 A1    Sep. 15, 2016

Related U.S. Application Data

(62) Division of application No. 13/322,616, filed as application No. PCT/US2010/036696 on May 28, 2010, now Pat. No. 9,272,083.
(Continued)

(51) Int. Cl.
*B01L 3/00* (2006.01)
*A61B 10/02* (2006.01)
(Continued)

(52) U.S. Cl.
CPC .......... *B01L 3/5021* (2013.01); *A61B 10/025* (2013.01); *A61M 1/3693* (2013.01);
(Continued)

(58) Field of Classification Search
CPC .......................... B01L 3/50215; A61M 5/3134
See application file for complete search history.

(56) References Cited

U.S. PATENT DOCUMENTS 3,814,248 A    6/1974  Lawhead
3,957,654 A    5/1976  Ayers
(Continued)

FOREIGN PATENT DOCUMENTS

EP    0 493 838 B1    7/1992
EP    1289618 B1      4/2001
(Continued)

OTHER PUBLICATIONS

"GPS III Platelet Separation System", *Biomet Biologics* (8 pages), no date given.
(Continued)

*Primary Examiner* — Timothy C Cleveland
(74) *Attorney, Agent, or Firm* — Hamilton, Brook, Smith & Reynolds, P.C.

(57) ABSTRACT

A system for separating components defining a cavity for receiving the fluid. The system further includes a rigid insert slidably disposed in the cavity, the insert including a funnel-shaped upper portion and a hole therethrough. The insert has a density such that upon centrifugation a selected component of the fluid resides within the upper portion of the insert. A bone marrow aspiration device includes an introducer needle assembly and an aspiration needle assembly. The introducer needle assembly includes an introducer cannula and a removable trocar. The aspiration needle assembly includes a flexible aspiration cannula and a flexible stylet. The length of the aspiration cannula is substantially greater than the length of the introducer cannula. The aspiration needle assembly is receivable in the introducer cannula when the trocar is removed from the introducer needle assembly. The
(Continued)

aspiration cannula forms a channel for aspirating bone marrow when the stylet is removed.

7 Claims, 22 Drawing Sheets

Related U.S. Application Data

(60) Provisional application No. 61/182,437, filed on May 29, 2009.

(51) Int. Cl.
*A61M 1/36* (2006.01)
*B01D 17/02* (2006.01)

(52) U.S. Cl.
CPC ...... *B01D 17/0217* (2013.01); *B01L 3/50215* (2013.01); *A61B 2010/0258* (2013.01); *A61M 2202/10* (2013.01); *B01L 3/50825* (2013.01); *B01L 2200/025* (2013.01); *B01L 2200/026* (2013.01); *B01L 2300/042* (2013.01); *B01L 2300/046* (2013.01); *B01L 2300/048* (2013.01); *B01L 2300/0609* (2013.01); *B01L 2300/0848* (2013.01); *B01L 2300/0851* (2013.01); *B01L 2300/0858* (2013.01); *B01L 2400/0478* (2013.01)

(56) References Cited

U.S. PATENT DOCUMENTS

| | | | |
|---|---|---|---|
| 4,001,122 A | 1/1977 | Griffin | |
| 4,152,270 A | 5/1979 | Cornell | |
| 4,818,418 A | 4/1989 | Saunders | |
| 4,844,818 A | 7/1989 | Smith | |
| 4,917,801 A | 4/1990 | Luderer et al. | |
| 4,939,087 A | 7/1990 | Van Wie et al. | |
| 5,030,341 A | 7/1991 | McEwen et al. | |
| 5,053,134 A | 10/1991 | Luderer et al. | |
| 5,236,604 A | 8/1993 | Fiehler | |
| 5,269,927 A | 12/1993 | Fiehler | |
| 5,271,852 A | 12/1993 | Luoma | |
| 5,308,506 A | 5/1994 | McEwen et al. | |
| 5,474,687 A | 12/1995 | Van Vlasselaer | |
| 5,489,386 A | 2/1996 | Saunders | |
| 5,577,513 A | 11/1996 | Van Vlasselaer | |
| 5,641,622 A | 6/1997 | Lake et al. | |
| 5,739,033 A | 4/1998 | Soon-Shiong | |
| 5,840,502 A | 11/1998 | Van Vlasselaer | |
| 6,051,146 A | 4/2000 | Green et al. | |
| 6,123,655 A | 9/2000 | Fell | |
| 6,221,315 B1 | 4/2001 | Giesler et al. | |
| 6,410,334 B1 | 6/2002 | Schmolz | |
| 6,516,953 B1 | 2/2003 | DiCesare et al. | |
| 6,596,179 B2 | 7/2003 | Giesler et al. | |
| 6,733,433 B1 | 5/2004 | Fell | |
| 7,077,273 B2 | 7/2006 | Ellsworth et al. | |
| 7,179,391 B2 | 2/2007 | Leach et al. | |
| 7,223,346 B2 | 5/2007 | Dorian et al. | |
| 7,316,932 B2 | 1/2008 | Woodside | |
| 7,374,678 B2 | 5/2008 | Leach et al. | |
| 7,445,125 B2 | 11/2008 | Ellsworth et al. | |
| 7,547,272 B2 | 6/2009 | Ellsworth et al. | |
| 7,514,075 B2 | 7/2009 | Hedrick et al. | |
| 7,585,670 B2 | 9/2009 | Hedrick et al. | |
| 7,595,043 B2 | 9/2009 | Hedrick et al. | |
| 7,598,089 B2 | 10/2009 | Collins | |
| 7,780,860 B2 | 8/2010 | Higgins et al. | |
| 7,832,566 B2 | 11/2010 | Leach et al. | |
| 7,845,499 B2 | 12/2010 | Higgins et al. | |
| 7,914,689 B2 | 3/2011 | Higgins et al. | |
| 7,954,646 B2 | 6/2011 | Leach et al. | |
| 7,992,725 B2 | 8/2011 | Leach et al. | |
| 8,048,321 B2 | 11/2011 | Leach et al. | |
| 8,048,678 B2 | 11/2011 | Duffy, Jr. et al. | |
| 8,062,534 B2 | 11/2011 | Higgins et al. | |
| RE43,547 E | 7/2012 | Ellsworth et al. | |
| 9,272,083 B2 | 3/2016 | Duffy et al. | |
| 2002/0006360 A1 | 1/2002 | Neal et al. | |
| 2003/0205538 A1 | 11/2003 | Dorian et al. | |
| 2005/0109716 A1 | 5/2005 | Leach et al. | |
| 2006/0273049 A1 | 12/2006 | Leach et al. | |
| 2006/0273050 A1 | 12/2006 | Higgins et al. | |
| 2006/0278588 A1 | 12/2006 | Woodell-May | |
| 2007/0131612 A1 | 6/2007 | Duffy et al. | |
| 2007/0265558 A1 | 11/2007 | Kleinbloeseum et al. | |
| 2008/0171951 A1 | 7/2008 | Fell | |
| 2009/0186065 A1 | 7/2009 | Tillman et al. | |
| 2009/0283524 A1 | 11/2009 | Ellsworth et al. | |
| 2010/0140182 A1 | 6/2010 | Chapman et al. | |
| 2010/0256595 A1 | 10/2010 | Leach et al. | |
| 2011/0056893 A1 | 3/2011 | Leach et al. | |
| 2011/0168193 A1 | 7/2011 | Leach et al. | |
| 2012/0015796 A1 | 1/2012 | Leach et al. | |
| 2013/0079212 A1 | 3/2013 | Ellsworth et al. | |
| 2016/0008808 A1 | 1/2016 | Levine et al. | |

FOREIGN PATENT DOCUMENTS

| | | |
|---|---|---|
| WO | WO 01/83068 A1 | 11/2001 |
| WO | WO 2003/099412 A1 | 12/2003 |
| WO | WO 2010/138895 A2 | 12/2010 |
| WO | WO 2014/120797 A1 | 8/2014 |

OTHER PUBLICATIONS

International Preliminary Report on Patentability dated Dec. 8, 2011 from International Application No. PCT/US2010/036696 filed on May 28, 2010.

International Search Report and the Written Opinion of the International Searching Authority dated Aug. 18, 2011 from International Application No. PCT/US2010/036696 filed on May 28, 2010.

International Search Report and the Written Opinion of the International Searching Authority from International Application No. PCT/US2014/013636, "Cell Concentration Devices and Methods," dated Jun. 4, 2014.

Joupperi, et al., "Isolation of Bone Marrow-Derived Stem Cells Using Density-Gradient Separation", *Exp. Hematol*, 35(2): 335-341 (Feb. 2007).

"RES-Q60 BMC Bone marrow concentrate", retrieved on May 4, 2010 from Thermogenesis Website URL: http://www.thermogenesis.com/CMSFiles/Pdf/Literature/resqbmc.pdf.

"RES-Q60 BMC Point-of-Care Automated Cell Capturing System", from TotipotentSC Corporate Website URL: http://totipotentsc.com/products/RES-Q60M_V2.pdf.

Zhang, et al., "Isolating and Culturing Rat Marrow Mesenchymal Stem Cells and Studying their Phenotypical and Functional Properties", *Sichuan Da Xue Xue Bao Yi Xue Ban*. 34(4): 738-741 (Oct. 2003). Abstract Only.

International Preliminary Report on Patentability from International Application No. PCT/US2014/013636, titled "Cell Concentration Devices and Methods," dated Aug. 4, 2015.

NonFinal Office Action, U.S. Appl. No. 14/764,115, entitled: "Cell Concentration Devices and Methods," dated Mar. 9, 2018.

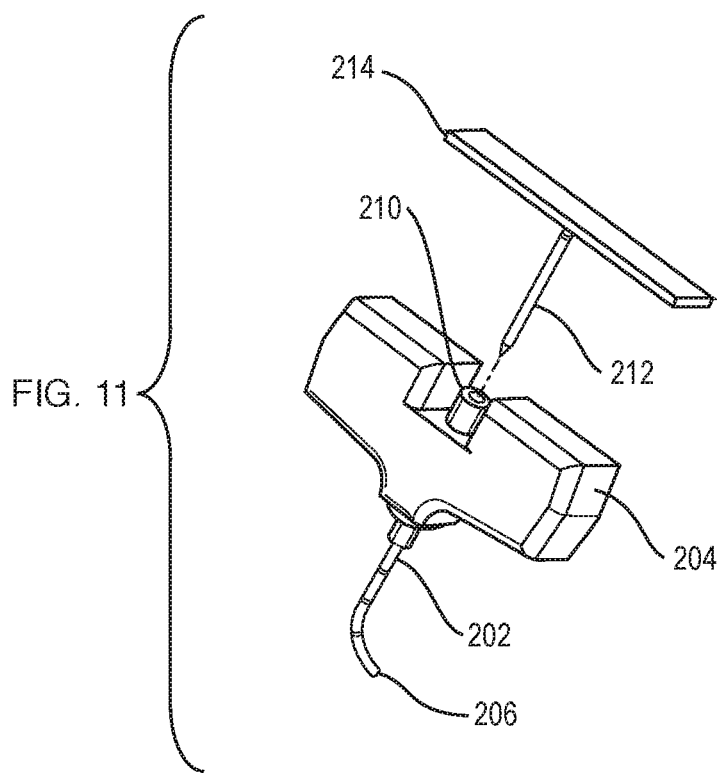

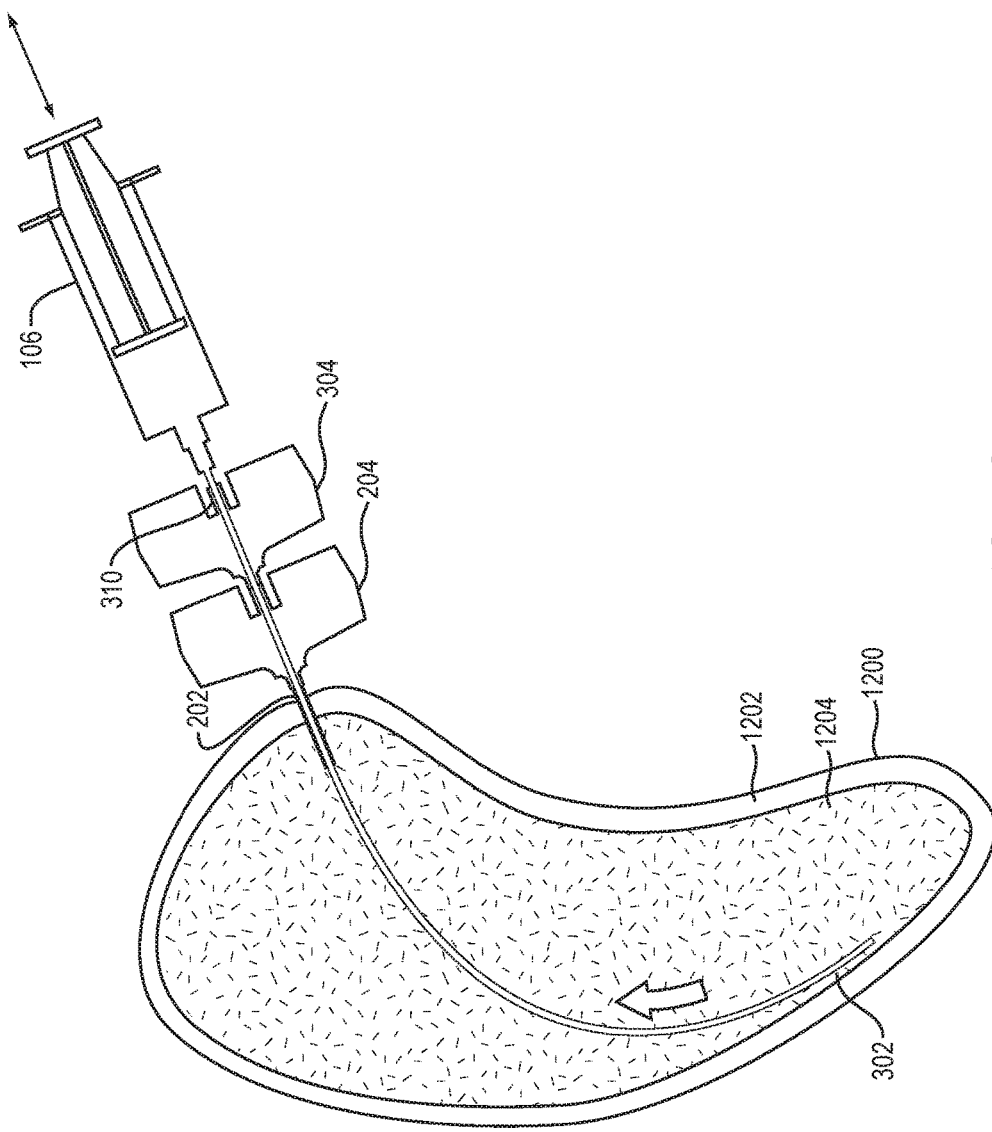

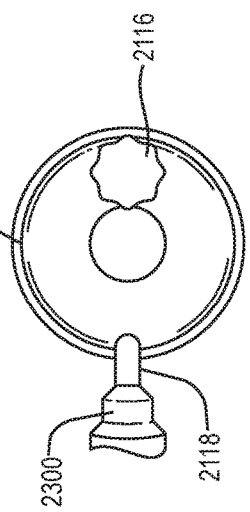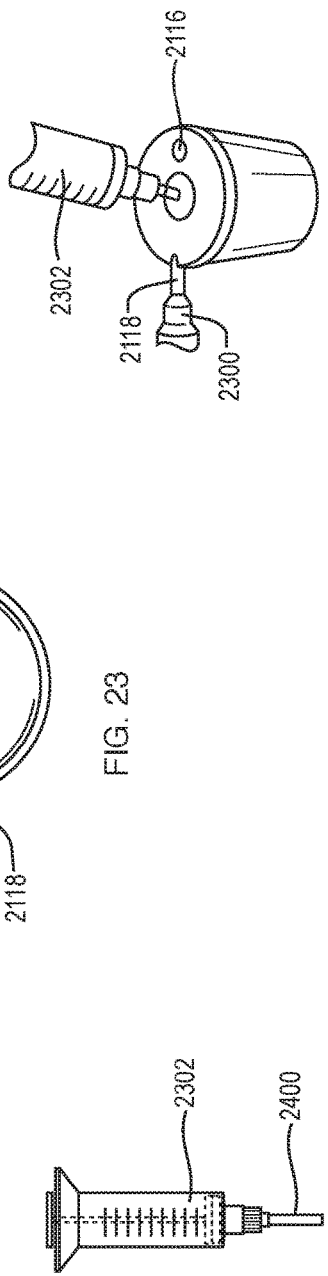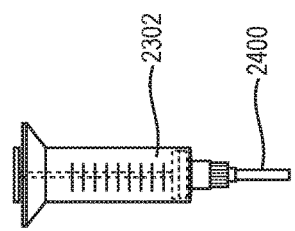

APPARATUS AND METHODS FOR ASPIRATING AND SEPARATING COMPONENTS OF DIFFERENT DENSITIES FROM A PHYSIOLOGICAL FLUID CONTAINING CELLS

RELATED APPLICATIONS

This application is a divisional of U.S. application Ser. No. 13/322,616 filed Nov. 28, 2011, which is the U.S. National Stage of International Application No. PCT/US2010/036696, filed May 28, 2010, which designates the U.S., published in English, and claims the benefit of U.S. Provisional Application No. 61/182,437, filed on May 29, 2009. The entire teachings of the above applications are incorporated herein by reference.

TECHNICAL FIELD

This invention relates to methods and apparatus for the aspiration of a fluid tissue and separation of the fluid tissue into different components of different densities. The invention has particular utility for the separation of bone marrow aspirate, adipose tissue and blood.

BACKGROUND OF THE INVENTION

Surgeons who must cut through tissue to gain access to tissue create surgical trauma. The ability to access subcutaneous tissue with minimal trauma is a benefit to the clinician and patient. With the aging population and rising health care costs, any therapy that is less invasive, more effective, and less expensive has the potential to change the practice of medicine. Surgeons are continually looking for means to gain access to a broad cross section of tissue with as little cutting as possible.

The emerging field of regenerative medicine is becoming more prevalent. This field will require percutaneous access to a broad cross section of sub-dermal tissue to not only source cells but to also deliver therapy. For example, clinical trials that are underway or have been completed are documenting the clinical benefit of delivering stem cells from bone marrow and fat for numerous different disease states to include cardiac disease, vascular disease and bone and orthopedic disorders.

One tissue that is commonly used as a source of stem cells in the emerging field of regenerative medicine is bone marrow aspirate. Historically, marrow aspirate has been combined with matrix scaffold material to help form bone. Accessing bone marrow aspirate from the hip is cumbersome and time consuming.

Today, most marrow aspiration is performed to obtain a biopsy sample to determine if a person has a disease of the blood or marrow. Volumes required for the histology to make these determinations are less than 2 mL. Consequently, most marrow aspiration needles are designed to only capture enough volume for these kinds of tests from the iliac bone in the hip. Techniques exist for drawing large volumes of marrow for procedures such as bone marrow rescue therapy in cancer treatment, but drawing large volumes is not frequently done and is being replaced by stem cell harvesting from mobilized peripheral blood (that is to say, peripheral blood harvested after treatment with growth factors or other chemicals which stimulate a rise in the number of hematopoietic progenitor cells in the peripheral blood).

The volumes typically used for bone grafting cell therapy in support of regenerative medicine are greater than required for biopsy but less than required for bone marrow rescue therapy. The typical range of volumes for mixing marrow aspirate with bone scaffold matrix material is from 5 mL to 10 mL.

The typical volume of marrow aspirate for point of care cell therapy is between 50 mL and 400 mL. Marrow aspirate for use in cell therapy is typically volume reduced by 80% or more in an effort to concentrate the stem cells from the sample.

Marrow aspiration is usually obtained from the iliac crest bone. Bone is made up of a hard outer core known as cortical bone and a soft spongy interior known as trabecular bone with marrow filling in the porous space within the spongy bone.

Currently, to draw larger volumes of marrow, clinicians usually go into the hip bone through the iliac crest. The goal is to penetrate deep into the spongy bone and then to withdraw small aliquots of marrow as the needle is withdrawn. Traditionally, marrow aspiration is performed with an aspiration needle 100 (FIG. 1). This needle has two basic components: a component comprising a handle 104 with a luer connector 110 for attaching a syringe 106 on one end and a hollow metal tube or cannula 102 on the other end; and a component (not shown in FIG. 1) comprising a second handle attached to a solid metal rod or trocar with a sharp pointed tip. The trocar of the marrow aspiration needle is removable. When assembled, the second handle fits over the first handle and the trocar fits through the cannula 102, including the luer connector 110 and handle 104, such that the pointed tip of the trocar extends past the distal end of the cannula 102. This entire needle assembly is often referred to as a JAMSHIDI® aspiration needle. To perform a marrow aspiration, a clinical practitioner uses the fully assembled needle to penetrate cortical bone 110 using the point of the trocar. The clinician uses hand pressure or a mallet to tap the assembled aspiration needle through the bone. The cannula and trocar are usually made of stainless steel or titanium. The assembled aspiration needle is very hard and stiff so that the needle will not bend or buckle when longitudinal force is applied against the proximal handle to allow it to penetrate the cortical bone. Once the hard cortical bone 112 is penetrated, the assembled needle easily advances through the trabecular bone, including spongy marrow, 114. During insertion, the trocar is left in place to prevent the hollow cannula from becoming clogged with debris as the needle is pushed through the spongy marrow. Once the needle assembly is advanced sufficiently into the trabecular bone 112, the trocar, including the trocar handle, is removed to expose the luer connector 110. Luer connector 108 of syringe 106 is attached to the luer connector 110 of the needle and a vacuum created by pulling the syringe plunger will remove the marrow (FIG. 1). Marrow aspirate is pulled through the distal end of the cannula 102 and into the syringe 106 as the needle 100 is slowly removed from the marrow space 114.

A traditional bone marrow aspiration needle is typically used to access marrow from the hip or iliac bone. Because the traditional aspiration needle is stiff, the needle can only advance linearly within the marrow space. Thus, clinicians often need to perform multiple punctures in order to gain larger volumes of aspirate from a more diverse cross section of the marrow space. Since the hip bone is long and thin, once the traditional aspiration needle has penetrated cortical bone, the sharp and stiff instrument has the potential to penetrate through the other side of the cortical bone, resulting in significant trauma. Consequently, it is important for the surgeon to have a proper angle and skilled technique to ensure a safe aspiration. Since the iliac crest curves from the front to the back of the patient, the best angle of entry is from the back. Since the trocar is made of a stiff material, once inside the spongy bone, the needle assembly can only go straight, thus requiring multiple punctures to obtain the required volume of aspirate.

A traditional marrow aspiration needle is meant to access bone marrow from larger cavities and is not ideally suited to drawing marrow from the smaller confines such as the vertebral body of the spine. Because of the sharpness and stiffness of a traditional aspiration needle, using such an instrument in the small curved marrow space of a vertebral body would greatly increase the likelihood of introducing trauma. Less invasive and safer methods to access the marrow tissue of the vertebral body are needed in an effort to support the emerging field of orthobiologics. One fast growing area of this field combines marrow aspirate with synthetic matrix material in order to facilitate instrumented assisted spinal fusion.

Once fluid tissue is aspirated or otherwise sourced, the next step is to separate the nucleated cells that are present in the fluid tissue and concentrate them into a small volume so that they can be used clinically. For example, there are several commercial devices to separate and concentrate nucleated cells from aspirated bone marrow, fat, or cord blood. Some of these systems employ a floating insert or buoy that is meant to create an interface between the separated fluid components or fractions of interest. The challenge for any apparatus designed to accomplish such a task is the ability to volume reduce the fluid in which the nucleated cells are suspended while recovering as many cells as possible. For example, in marrow aspirate, approximately 1 to 2 percent of the cells suspended in the fluid are the target nucleated cells. Currently, no commercial device is able to consistently capture high percentages of nucleated cells while at the same time efficiently volume reduce (i.e, concentrate) the beginning fluid. In other words, no current device is able to simultaneously obtain a high yield and a high final concentration.

Therefore, a need exists for a bone marrow aspiration and separation system that can reduce or minimize the aforementioned problems.

SUMMARY OF THE INVENTION

A bone marrow aspiration device includes an introducer needle assembly and an aspiration needle assembly. The introducer needle assembly includes an introducer cannula having a proximal end and a distal end, each end including an opening, an introducer handle connected to the proximal end of the introducer cannula, and a removable trocar. The trocar has a proximal end and a distal end and extends through the introducer cannula from the cannula handle. The distal end of the trocar extends beyond the distal end of the introducer cannula and includes a sharp tip to penetrate bone. The aspiration needle assembly includes a flexible aspiration cannula having a proximal end and a distal end, each end including an opening, an aspiration handle connected to the distal end of the aspiration cannula, and a flexible stylet. The length of the aspiration cannula is substantially greater than the length of the introducer cannula. The stylet has a proximal end and a distal end and extends through the aspiration cannula from the aspiration handle, the distal end of the stylet extending beyond the distal end of the aspiration cannula. The aspiration needle assembly is receivable in the introducer cannula when the trocar is removed from the introducer needle assembly. The aspiration cannula forms a channel for aspirating bone marrow when the stylet is removed.

In one embodiment, the stiffness of the assembled introducer cannula and trocar is sufficiently high to allow the introducer cannula and trocar to penetrate cortical bone when a longitudinal force is applied to the introducer cannula and trocar in a distal direction. The stiffness of the assembled aspiration cannula and stylet can be sufficiently high to allow the aspiration cannula and stylet to penetrate bone marrow when a longitudinal force is applied to the aspiration cannula and stylet in a distal direction. The stiffness of the assembled aspiration cannula and stylet can be sufficiently low to not allow the aspiration cannula and stylet to penetrate cortical bone but to flex or bend when a longitudinal force is applied to the aspiration cannula and stylet in a distal direction. The introducer cannula may be substantially straight when the trocar extends through the introducer cannula, but may revert to a preset bend when the trocar is removed.

A method for aspirating bone marrow includes inserting an aspiration needle assembly into bone marrow through an introducer cannula placed in a bone, the aspiration needle assembly including a flexible aspiration cannula and a flexible stylet, removing the stylet from the aspiration needle assembly, the aspiration cannula forming a channel for aspirating bone marrow when the stylet is removed, and aspirating bone marrow through the channel. The aspiration cannula has a proximal end and a distal end, each end including an opening, the length of the aspiration cannula being substantially greater than the length of the introducer cannula. The aspiration needle assembly further includes an aspiration handle connected to the proximal end of the aspiration cannula. The flexible stylet has a proximal end and a distal end, the stylet extending through the aspiration cannula from the aspiration handle, the distal end of the stylet extending beyond the distal end of the aspiration cannula.

In an embodiment, inserting the aspiration needle assembly includes flexing or bending the aspiration cannula and stylet against cortical bone. Furthermore, aspirating bone marrow can include retracting the aspiration needle assembly from the bone.

A system for separating components of different densities from a physiological fluid containing cells using a centrifuge includes a container, having a bottom, a top disposed opposite the bottom, and a sidewall extending between the bottom and the top, the container defining a cavity for receiving the fluid. The system further includes a rigid insert slidably disposed in the cavity, the insert including a funnel-shaped upper portion and a hole therethrough. The funnel-shaped upper portion need not be conical and need not be symmetric. The hole may be centered in the insert or may be offset. The insert has a density such that upon centrifugation a selected component of the fluid resides within the upper portion of the insert. Also included is a port disposed in the top of the container and a cannula assembly receivable in the port to butt against the insert and withdraw the selected component.

In one embodiment, the cannula assembly includes a closed end to close the hole in the insert and a side port to withdraw the selected component. The cannula assembly may include an inner cannula coaxially disposed within an outer cannula and first set of side ports into the cannulae to open a first channel through the cannula assembly for withdrawing the selected component from the upper portion of the insert with alignment of the first set of ports with relative rotation of the inner and outer cannulae. The cannula assembly may include a second set of side ports into the cannulae to open a second channel through the cannula assembly for withdrawing a component other than the selected component with alignment of the second set of ports with relative rotation of the inner and outer cannulae.

In an embodiment, the selected component is buffy coat and the component other than the selected component is blood plasma. In one embodiment, the volume contained in the funnel-shaped upper portion is between 5% and 20% of the volume of the container cavity The system may include a clamping mechanism to hold the insert in place after centrifugation, wherein the clamping mechanism is coupled to the container sidewall to press the sidewall inward against the insert.

Another system for separating components of different densities from a fluid containing cells using a centrifuge includes a container having a top, a sidewall extending from the top, and a movable bottom in sealing engagement with the sidewall, the container defining a cavity for receiving the fluid. The system further includes a rigid insert slidably disposed in the cavity and defining a lumen through the insert, the lumen including a hole and a funnel-shaped upper portion in fluid communication with the hole. The funnel-shaped upper portion need not be conical and need not be symmetric. The hole may be centered in the insert or may be offset. The insert has a density selected such that upon centrifugation a selected component of the fluid resides within the lumen. The system also includes a first port disposed adjacent the top of the container for withdrawing a fluid component having a lower density than the selected component, the first port being closed by the insert with upward movement of the insert and movable bottom. Also included is a cannula for withdrawing the selected component from the lumen of the insert.

In one embodiment, volume contained in the lumen is between 5% and 20% of the volume of the container cavity. The system can include a second port disposed in the top of the container for inserting the cannula. In another embodiment, the cannula includes a proximal end attached to the top of the container and a distal end extending into the container. The cannula may include a side port to withdraw the selected component from the funnel-shaped upper portion of the insert, the distal end of the cannula being closed and adapted to mate with the insert to close the hole in the insert with upward movement of the insert. In one embodiment, the lumen of the insert comprises multiple holes.

A method of separating components of different densities from a fluid containing cells using a centrifuge includes receiving the fluid in a separation system, the system including a container, having a bottom, a top disposed opposite the bottom, and a sidewall extending between the bottom and the top, the container defining a cavity for receiving the fluid. The system further includes a rigid insert slidably disposed in the cavity, the insert including a funnel-shaped upper portion and a hole therethrough, the insert having a density such that upon centrifugation a selected component of the fluid resides within the upper portion of the insert. The system also includes a port disposed in the top of the container. The method further includes applying centrifugal force to the system, inserting a cannula assembly into the container through the port and withdrawing the selected component with the cannula assembly.

In one embodiment, the method includes closing the hole in the insert with a closed end of the cannula assembly, the cannula assembly including a side port to withdraw the selected component. The method may further include opening a first channel through the cannula assembly and withdrawing the selected component through the first channel. The cannula assembly can include an inner cannula coaxially disposed within an outer cannula and a first set of side ports into the cannulae to open the first channel with alignment of the first set of ports with relative rotation of the inner and outer cannulae. The method may further include opening a second channel through the cannula assembly and withdrawing the component other than the selected component through the second channel. The cannula assembly can include a second set of side ports into the cannulae to open the second channel with alignment of the second set of ports with relative rotation of the inner and outer cannula.

In an embodiment, the method includes, with a clamping mechanism, holding the insert in place after centrifugation.

A method of separating components of different densities from a fluid containing cells using a centrifuge includes receiving the fluid in a separation system, the system including a container, having a top, a sidewall extending from the top, and a movable bottom in sealing engagement with the sidewall, the container defining a cavity for receiving the fluid. The separation system further includes a rigid insert slidably disposed in the cavity and defining a lumen through the insert, the lumen including a hole and a funnel-shaped upper portion in fluid communication with the hole, the insert having a density selected such that upon centrifugation a selected component of the fluid resides within the lumen. The separation system also includes a first port disposed adjacent the top of the container. The method further includes applying centrifugal force to the system and, after centrifugation, withdrawing a fluid component having a lower density than the selected component through the first port, thereby moving the insert and movable bottom upward. The method also includes, with the insert, closing the first port with upward movement of the insert and movable bottom; and with a cannula, withdrawing the selected component from the lumen of the insert after upward movement of the insert and movable bottom.

In an embodiment, withdrawing the selected component includes inserting the cannula into the lumen of the insert through a second port disposed in the top of the container.

In an embodiment, the method further includes closing the hole in the insert with a closed distal end of the cannula, the closed distal end of the cannula extending into the container and being adapted to mate with the insert with upward movement of the insert, the cannula including a proximal end attached to the top of the container and a side port, and withdrawing the selected component through the side port in the cannula from the funnel-shaped upper portion of the lumen.

Embodiments of the current invention overcome the limitations of known devices for aspiration and concentration of cells from marrow or other tissue. With respect to the disclosed aspiration system, the combination of an introducer needle assembly and a flexible aspiration needle assembly allows for one puncture of the cortical bone to access a broader volume of marrow from which to harvest cells. With respect to the disclosed separator devices, the insert does not form a closed recess or a depression or indent to capture cells, but rather allows for the natural sedimentation of the fluid within the container and through the insert. The insert has at least one relatively large through hole or channel, including a funnel-shaped upper portion, that allows for the free flow of fluid within the container and through the insert and does not interfere with the natural layering of different density components of the fluid. In addition, the insert identifies the location of a layer of interest, including the target cells. The funnel-shaped upper portion and the through hole reduce the cross-sectional area and increase the thickness of the layer of interest. This facilitates extraction of the target cells and contributes to a high yield and high concentration of the target cells.

Embodiments of the current invention overcome limitations of other systems that use inserts or buoys without a through hole and where the fluid path under centrifugation is confined to the distance between the inner wall of a container or tube and the outer walls of the inserts or buoys. In those systems, minor clots, particles, or other inconsistencies in the fluid can lodge between the walls of the tube and the buoys interfering with the natural layering of the different density components of the fluid.

The insert includes a density selected such that after centrifugation the target cells reside within the hole, the funnel-shape upper portion, or lumen defined by the insert. Under gravitational force the insert floats freely within the container with substantially all of the fluid flowing through the hole or lumen of the insert, but not between the outer wall of the insert and the inner wall of the container. The distance between the inner wall of the container and the outer wall of the insert creates enough space to allow the insert to move freely within the container.

The apparatus and method to access and source, e.g., aspirate, tissue includes separate needle assemblies of different lengths such that when the trocar from the first shorter needle assembly is removed the second longer needle assembly fits coaxially through the cannula of the first needle assembly. The first or introducer needle assembly can have a stiffness that is adequate to penetrate surface tissue, e.g., skin and cortical bone, to gain access to the target tissue, e.g., bone marrow. The second needle assembly has a stiffness that is adequate to penetrate tissue that is soft relative to the stiffness of the first needle assembly, but not tissue that is hard. For example, the second or aspiration needle assembly can be designed to bend and not pierce the inner anatomical structures comprised of tissue that hard relative to the stiffness of the needle assembly, such as cortical bone.

Once the tissue is sourced, the tissue can be loaded into a separation device that can be centrifuged. Upon centrifugation, the target cells naturally sediment into the through hole or lumen of the floating insert. These cells are then isolated by means of a cannula. The closed end of the cannula can close the hole in the insert. The target cells residing in the hole of lumen of the floating insert may be sealed from fluid below while fluid above the insert is removed through a cannula.

The combination of the aspiration and concentration apparatus allows a clinician the ability to access subcutaneous tissue in a less traumatic manner and then concentrate nucleated cells from that tissue aspirate. The two apparatus can be combined by means of tubing and fluid ports, including luer connections, to create a total solution from aspiration to concentration.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 11 is a perspective view of an embodiment of an introducer needle assembly with a preset bend in the cannula after removal of the trocar.

FIGS. 12A-C are a series of sequential diagrams illustrating aspiration of bone marrow from a hip bone according to an embodiment of the invention. FIG. 12A shows the introducer needle assembly penetrating cortical bone. FIG. 12B shows insertion of the flexible aspiration needle assembly through the introducer cannula into bone marrow. FIG. 12C shows the aspiration of bone marrow through the flexible aspiration cannula into a syringe connected to the handle of the aspiration cannula.

FIG. 21 is perspective view of an alternative embodiment of a separation system that includes a container with a movable bottom or plunger.

FIG. 22 is a top view of the separation system of FIG. 21.

FIG. 23 is a top view of the separation system of FIG. 21 illustrating connection of a first syringe to a first port.

FIG. 24 is a side view of a cannula connected to a second syringe for insertion into the container of the separation system of FIG. 21.

FIG. 25. is a perspective view of the separation system of FIG. 21 showing the first syringe connected to a first port and the cannula connected to a second syringe and inserted into the container through a second port.

DETAILED DESCRIPTION OF THE INVENTION

A description of example embodiments of the invention follows.

With respect to aspirating bodily fluids, an aspiration apparatus is provided that allows for different lengths of needle assemblies to fit coaxially together by removing the trocar or stylet of the previous needle assembly. The outer diameter of the cannula of each successive needle assembly is smaller and the length is longer than the inner diameter and length, respectively, of the cannula of the previous needle assembly. Beyond diameter and length, each successive needle assembly can have other characteristics such as flex and sharpness. Many different diameters, lengths, and stiffness can be incorporated into the design and the design can incorporate two or more needle assemblies in order to make apparatus designed for certain applications. For example, assemblies designed for use in tendon and ligament repair may be different in length, stiffness, or some other material property, such as lubricity, than those designed to be used in osteonecrosis. Assemblies designed to be used in pediatrics may be different in size than those used in an adult, to accommodate a smaller patient, but may also differ in stiffness to reflect potential differences in developing tissue as compared to adult tissue.

Figure 1:
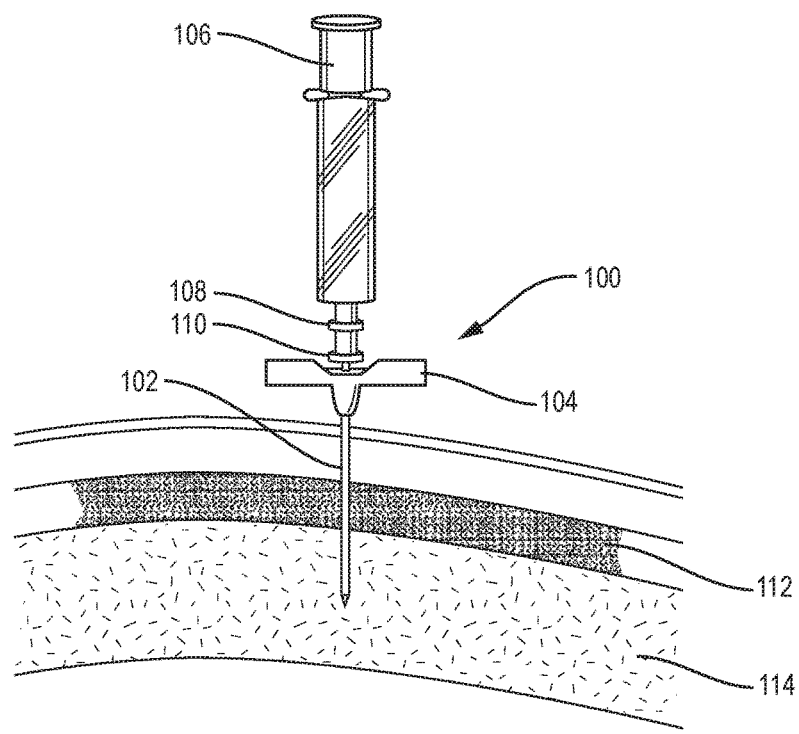
FIG. 1 illustrates bone marrow aspiration with a standard aspiration needle.
Figure 2:
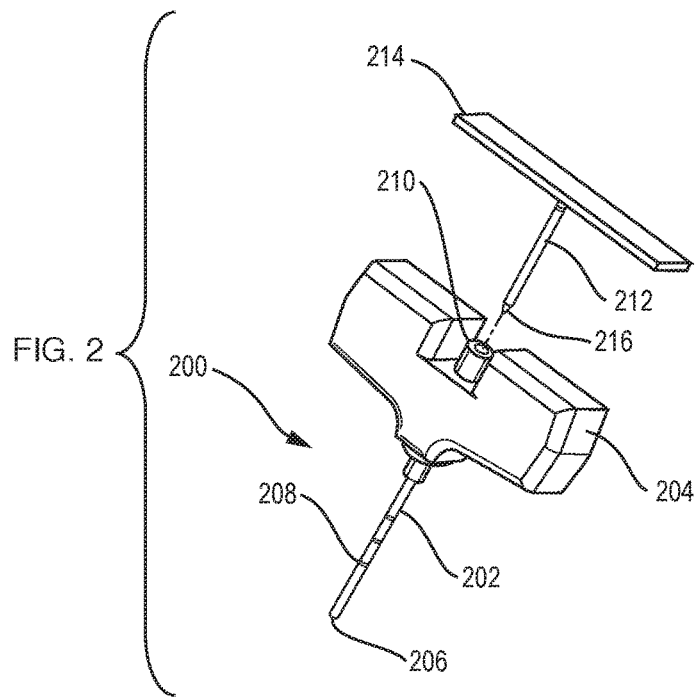
FIG. 2 is a perspective view of an embodiment of a introducer needle assembly showing the trocar removed from the introducer cannula.

As shown in FIG. 2, an introducer needle assembly 200 includes an introducer cannula 202 having a proximal end 206 and a distal end 210, each end including an opening, an introducer handle 204 connected to the proximal end of the introducer cannula, and a removable trocar 212. The trocar 212 has a proximal end and a distal end and fits into the introducer cannula 202. When inserted into the introducer cannula 202, the trocar 212 extends through the introducer cannula 202 from the cannula handle 204. The distal end of the trocar extends beyond the distal end of the introducer cannula and includes a sharp tip 216 to penetrate bone. The trocar may include a trocar handle 214 connected to the proximal end of the trocar. The introducer needle assembly 200 can include a luer connector at the distal end 210 of the cannula to which a syringe can be attached.

Figure 3:
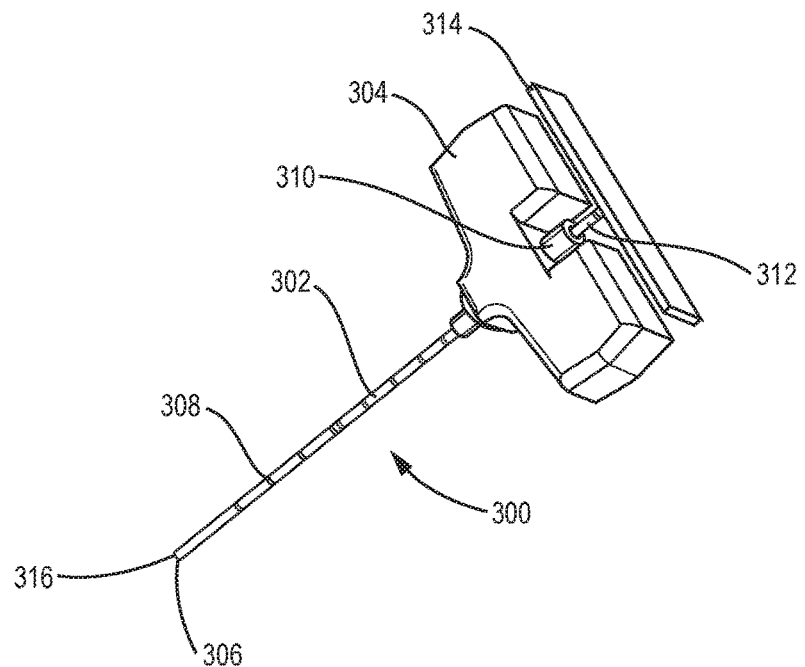
FIG. 3 is a perspective view of an embodiment of a flexible aspiration needle assembly.

As shown in FIG. 3, an aspiration needle assembly 300 includes a flexible aspiration cannula 302 having a proximal end 310 and a distal end 306, each end including an opening, an aspiration handle 304 connected to the distal end 310 of the aspiration cannula, and a flexible stylet 312. The length of the aspiration cannula 302 is substantially greater than the length of the introducer cannula 202 (FIG. 2). The stylet 312 has a proximal end and a distal end and extends through the aspiration cannula 302 from the aspiration handle 304, the distal end of the stylet extending beyond the distal end 306 of the aspiration cannula 302.

Figure 4:
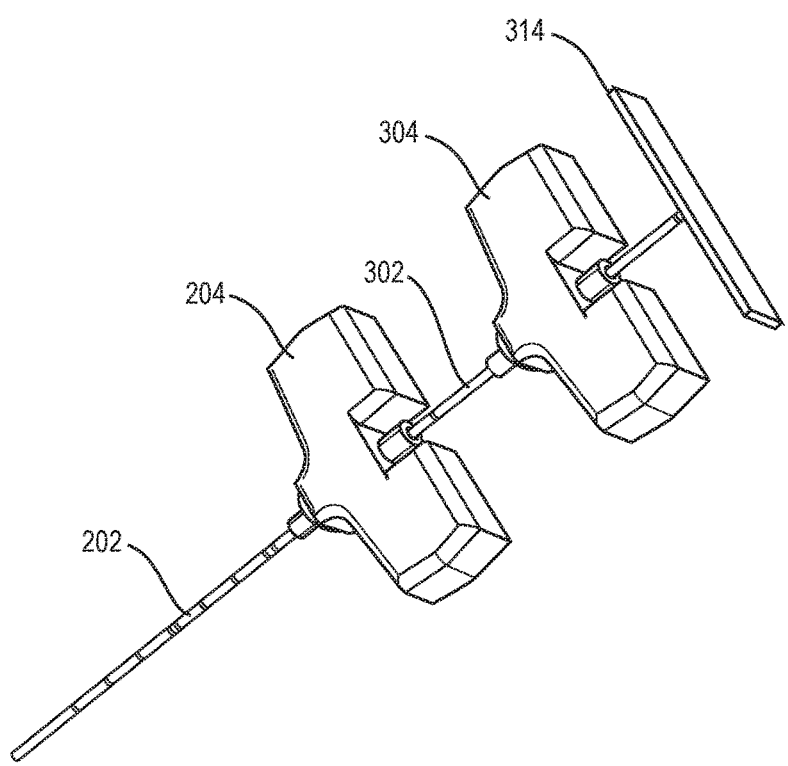
FIG. 4 is a perspective view of an embodiment of a flexible aspiration needle assembly partially inserted through an introducer needle assembly after the trocar has been removed.

As shown in FIG. 4, the aspiration needle assembly 300 is receivable in the introducer cannula 202 when the trocar 212 is removed from the introducer needle assembly 200.

Figure 5:
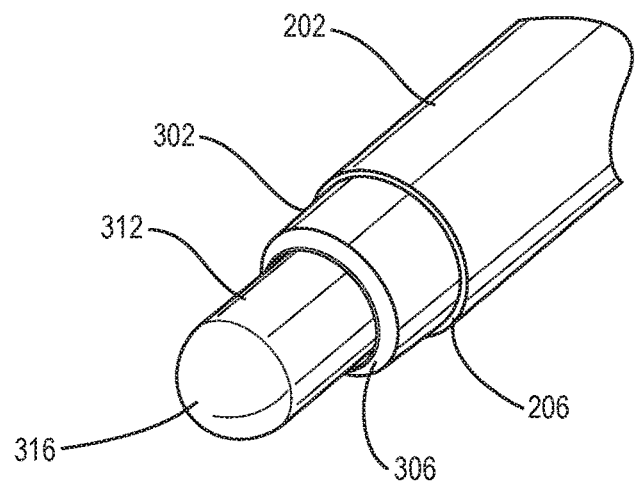
FIG. 5 is a perspective view of the distal end of the aspiration needle assembly extending through the distal end of the introducer cannula.

FIG. 5 is a close-up view showing the distal end 306 of the aspiration cannula 302 and the distal end of the stylet 312 coming out of and extending past the distal end 206 of the introducer cannula 202. The distal end of stylet 312 can include an atraumatic tip 316, such as a round or blunt tip. When fully inserted though introducer cannula 202, the stylet 312 and flexible cannula 302 will extend farther past the distal end 206 than shown in FIG. 5. This is so because of the length of the aspiration cannula 302 is substantially greater than the length of the introducer cannula 202.

Figure 6:
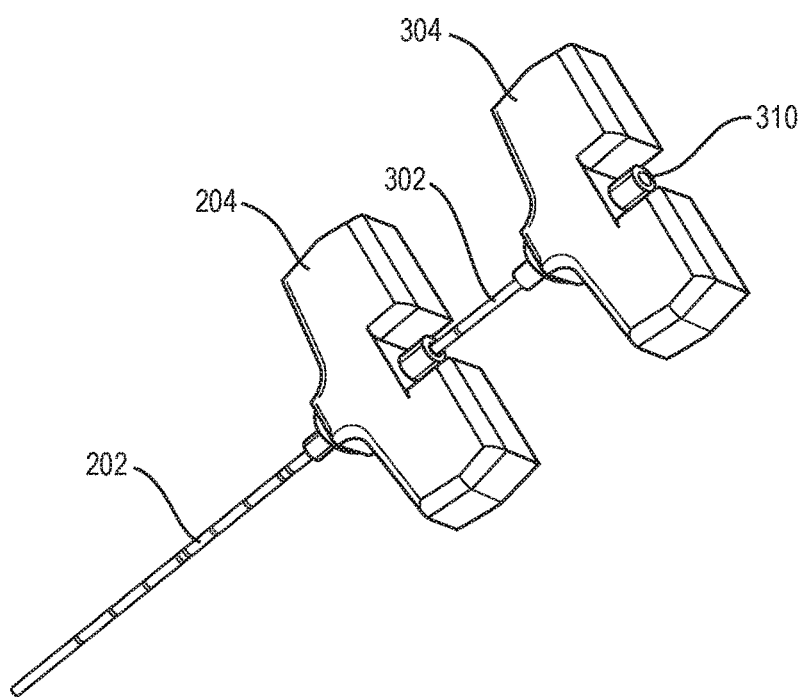
FIG. 6 is a perspective view of the introducer cannula and flexible aspiration needle assembly of FIG. 4 after the stylet has been removed.

As shown in FIG. 6, the aspiration cannula 302 forms a channel for aspirating fluid tissue, including bone marrow, when the stylet 312 is removed.

Figure 7:
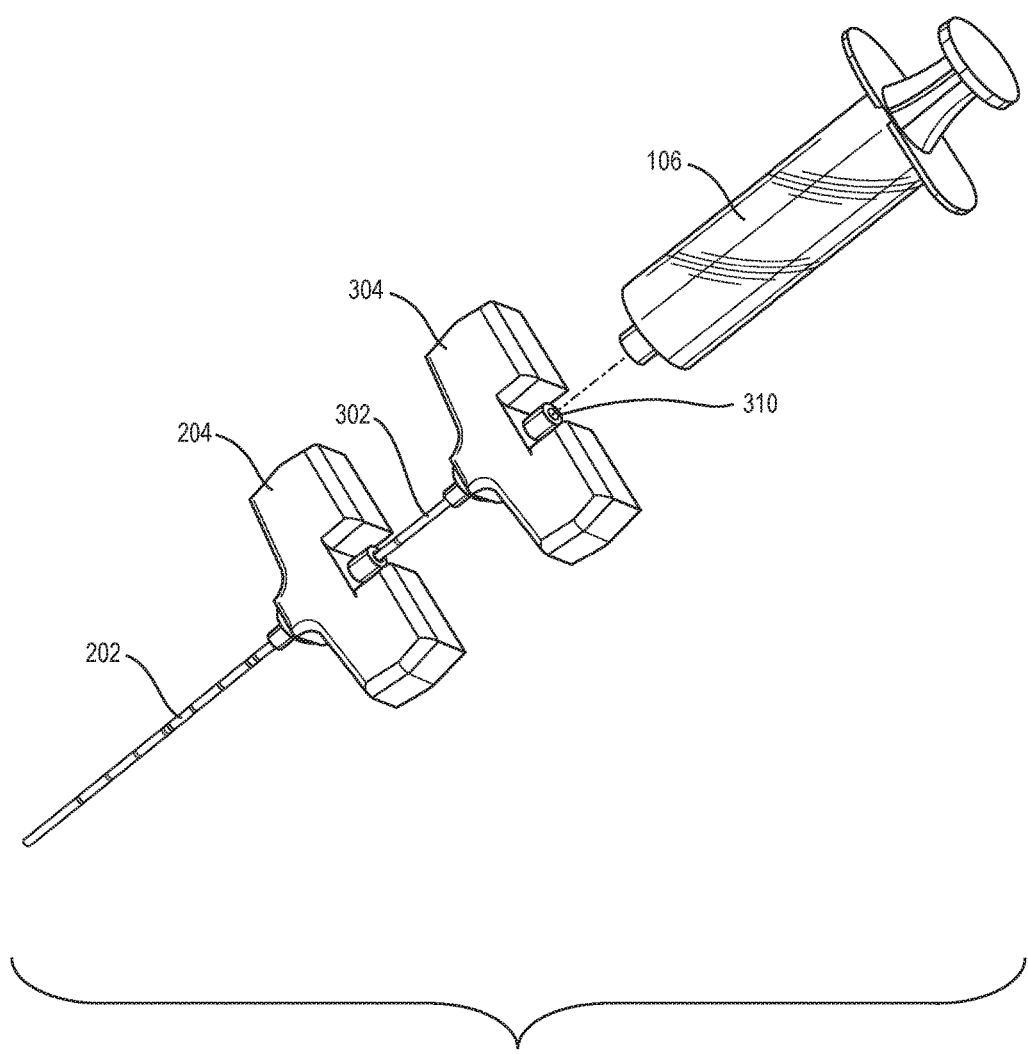
FIG. 7 is a perspective view of the introducer cannula and aspiration cannula of FIG. 6 and a syringe to be connected to the handle of the aspiration cannula.

As shown in FIG. 7, the aspiration needle assembly 300 can include a luer connector at the proximal end 310 of the aspiration cannula to which a syringe 106 can be attached after removal of the stylet 312.

Figure 8:
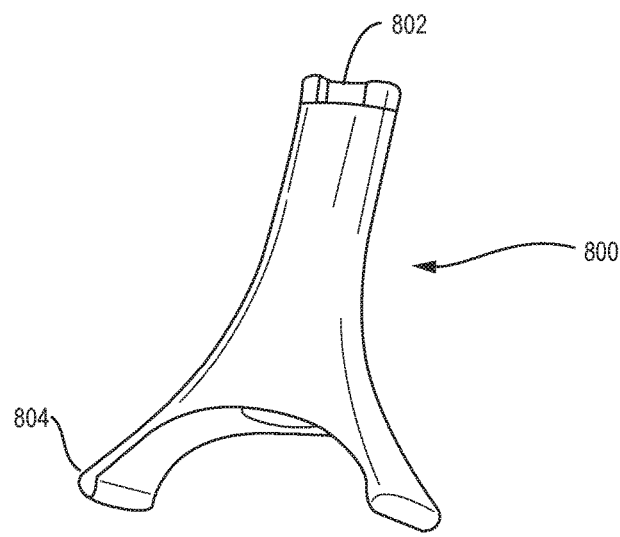
FIG. 8 is a perspective view of a guide that can be used to steer the introducer needle assembly of FIG. 2.

FIG. 8 shows a guide 800 that can be used to steer the introducer needle assembly. The guide 800 includes contoured elements 804 designed to fit over the outer bone containing marrow that is to be extracted at a desired entry point and with an appropriate entry angle. The introducer needle assembly 200 then passes through a channel 802 into the bone at the desired entry point and angle.

Figure 9:
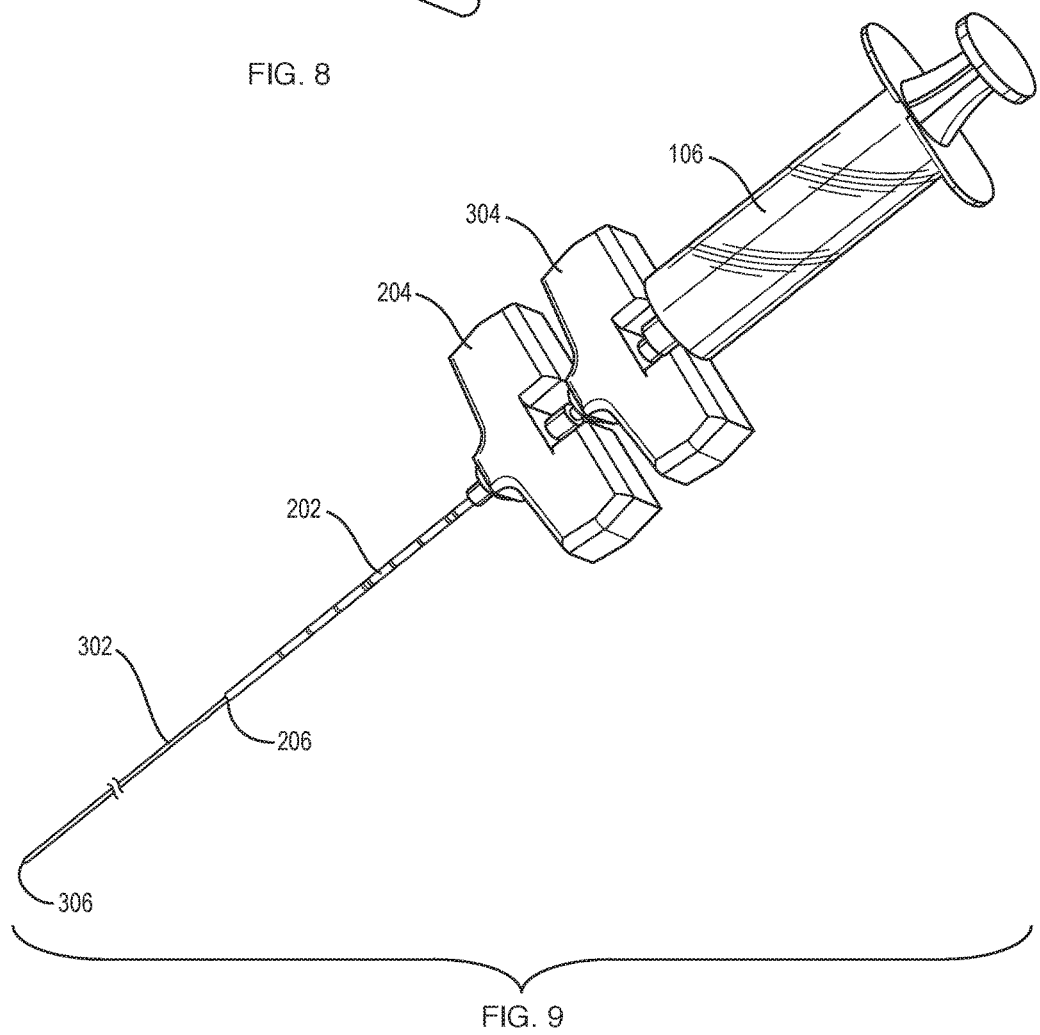
FIG. 9 is a perspective view of an embodiment of the assembled aspiration device showing the aspiration cannula deployed through the cannula and handle of the introducer needle assembly and a syringe connected to the aspiration needle assembly.

FIG. 9 shows the aspiration needle assembly 300 with a syringe 106 connected to the luer connector at the proximal end 310 of the aspiration cannula 302. The stylet 312 has been removed from the aspiration needle assembly 300, which extends through the introducer cannula 202. The distal end 306 of the aspiration cannula 302 substantially extends beyond the distal end 206 of the introducer cannula 202. When the distal end 306 of the aspiration cannula is placed in bone marrow, a fluid path exists from the marrow through the aspiration cannula 302 into the syringe 106. The vacuum pressure created by pulling the plunger of the syringe 106 will cause marrow fluid to travel though the fluid path. FIG. 9 shows the aspiration needle assembly 300 without flex or bend.

Figure 10:
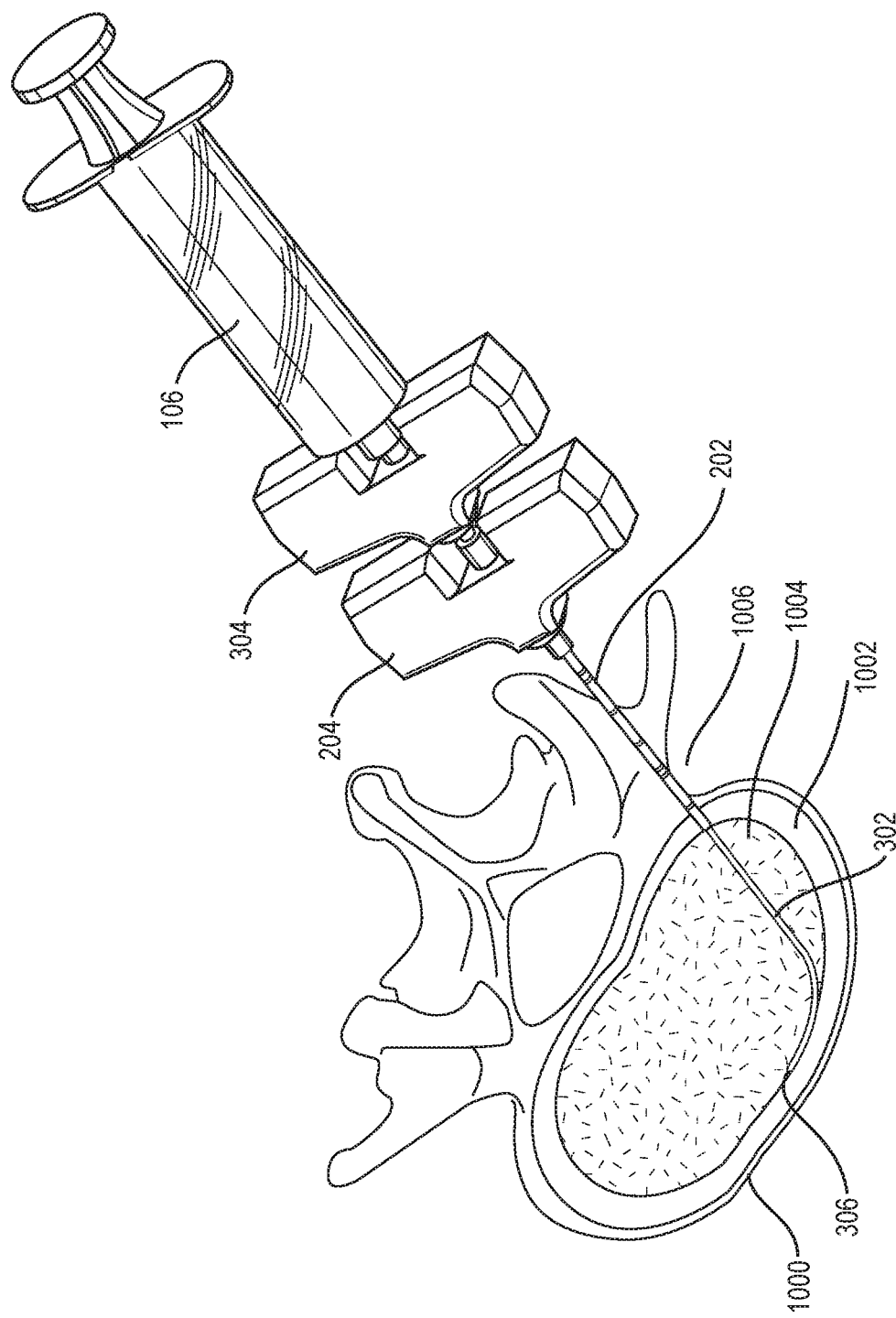
FIG. 10 is a perspective view of an embodiment of the aspiration device inserted into a vertebral body.

FIG. 10 is a perspective view of an embodiment of the aspiration device inserted into a vertebral body. Introducer needle assembly 200 has penetrated pedicle 1006 and cortical bone 1002 of vertebral body 1000. Trocar 202 has been removed, leaving introducer cannula 202 in place. Aspiration cannula 302 extends through the introducer cannula 202 and into bone marrow 1004. The stylet 312 has been removed from the aspiration needle assembly 300. A syringe 106 is connected to the luer connector at the proximal end 310 of the aspiration cannula 302. The distal end 306 of the aspiration cannula 302 substantially extends beyond the distal end 206 of the introducer cannula 202. The distal end 306 of the aspiration cannula is placed in bone marrow and a fluid path exists from the marrow through the aspiration cannula 302 into the syringe 106. The flexible aspiration assembly travels straight through the bone marrow 1004 until deflecting off the cortical bone 1002 opposite the point of entry into the vertebral body 1000. Upon hitting the cortical bone 1002, the aspiration cannula bends and travels along the inside of cortical bone 1002. Since the material of the aspiration needle assembly does not take a permanent shape, both the flexible stylet and aspiration cannula can be easily removed to perform the aspiration.

In the embodiment of an introducer needle assembly 200 shown in FIG. 2, the trocar 212 includes a tip 216 that is sharp and stiff so that it can penetrate hard tissue. In addition, the introducer assembly 200 can include a ratcheting mechanism. The trocar can have a tip 216 designed to allow the user to use hand pressure to ratchet the trocar 212 through the cortical bone as opposed to pushing the trocar through the bone. The trocar 212 can be combined with the handle and introducer cannula 202 to form a ratchet mechanism. This will allow the clinician to use hand pressure to twist in one direction to direct the trocar 212 and cannula 202 through the bone as opposed to pushing and twisting the introducer needle assembly 200 through the bone. The trocar 212 moves within the cannula 202, but can cut only when rotated in one direction (for example, when rotated clockwise but not counterclockwise). This is in contrast to standard aspiration needles, which cut when rotated in either direction. In addition, the introducer cannula 202, the aspiration cannula 302, or both can have markings 208, 308 (FIGS. 2 and 3) for gauging the depth of penetration of either cannula into bone tissue.

The introducer needle assembly 200 is short so it will provide better leverage. Also, with the aid of a ratcheting mechanism, it will allow for a controlled penetration. Because the introducer needle assembly 200 is short, the likelihood of going through the cortical bone after the initial penetration is minimized. For example, the greatest distance the short needle could penetrate the cortical bone may be set at approximately 2-3 cm. The distance may be set by the length of needle assembly 200.

The stylet 312 of the aspiration needle assembly 300 serves to prevent the aspiration cannula 302 from becoming clogged with tissue pieces as the aspiration needle assembly advances through tissue that is less stiff. In the case of bone marrow, the stylet 312 prevents the aspiration cannula 302 from becoming clogged with small particles of trabecular bone, fat, and endothelium as the needle assembly 300 advances through the spongy marrow space. The stylet 312 can include an atraumatic tip 316, such as a round or blunt tip. The stylet 312 can bend with the aspiration cannula 302 when the assembled stylet and cannula come into contact with tissue that is stiffer than the combined stiffness of stylet and cannula. Once the aspiration needle assembly 300 is advanced to the desired location or depth within the target tissue, the stylet needs to have sufficient flexibility so that when the clinician pulls back on the stylet handle, the stylet easily slides out of the aspiration cannula. By retrieving the aspiration cannula back along the path forged by the combined aspiration needle assembly, the clinician can deliver or aspirate material with the lumen of the cannula remaining unclogged.

Benefits of improved marrow aspiration are that the ability to mix marrow aspirate with graft material will improve the likelihood of successful bony fusion in instrumented spinal fusion. Concentrating the cells will improve outcomes even further. Several authoritative studies have demonstrated the osteogenic and osteoinductive properties of marrow aspirate.

Furthermore, a hole in the harder cortical bone made by the introducer needle assembly 200 can be used as a pilot hole to attach orthopedic hardware, such as pedicle screws for attaching a spinal cage. Combining the making of pilot holes for bone screws with marrow aspiration makes the process of placing bone screws more efficient. The ability of the aspiration needle assembly 300 to gauge the depth of the screw and complete the pilot hole through less dense spongy marrow will make the process of creating the pilot hole safer and more accurate. Eliminating the need to aspirate marrow with a traditional marrow aspiration needle 100 from the hip bone will save procedure time and associated cost. Having a tool that can combine multiple functions, aspirating and concentrating, will eliminate the amount of accessory tools the surgeon requires. Combining the drilling of pilot holes for bone screws with marrow aspiration and concentration will make the process very convenient for the clinician.

In the case of marrow aspiration from the iliac crest, if the general procedure performed from a posterior approach such as in spinal fusion (i.e. with the patient lying on side or stomach), accessing the iliac crest is generally not problematic. However, if the surgery is performed from an anterior position such as hip replacement (i.e., patient lying on back), then accessing the iliac crest is more problematic as the bone tends to curve from front to back. Surgeons often flip the patient to gain better access to the bone. As illustrated in FIG. 12, the bone marrow aspiration apparatus disclosed herein will allow safe access to the spongy bone from the front, because the shorter introducer needle assembly, such as introducer assembly 200, is not long enough to puncture the other side of the iliac bone. The longer aspiration needle assembly, such as assembly 300, does not have the strength to puncture cortical bone but will travel through marrow. Thus, iliac bone marrow aspirations can be performed when the patient is on his or her back, saving the inconvenience, cost, and additional safety and sterility complications of flipping the sedated patient.

Embodiments of the current invention can be used for bone marrow aspiration to allow a surgeon the ability to 1) access the iliac bone from an anterior position and 2) be able to draw larger volumes of marrow from along the narrow long cavity of the iliac bone and 3) reduce the risk of pushing the needle assembly through the other side of the bone and causing unnecessary trauma and 4) reducing the number of punctures needed to get a volume of marrow.

In one embodiment shown in FIG. 11, the introducer cannula 202 has a preset bend. The introducer cannula 202 is substantially straight when the trocar 212 extends through the introducer cannula, but upon removal of the trocar 212, the introducer cannula 202 reverts to the preset bend. The introducer cannula 202 having a preset bend may include a shape memory metal, such as nickel titanium. The introducer cannula 202 may be short and may be moved, e.g., rotated, once inserted into the bone. The introducer cannula 202 with a preset bend may be rotated to cause an aspiration needle assembly 300 that extends through the introducer cannula 202 to take a preset direction in the marrow space.

A feature of the aspiration needle assembly 300 is that its persistence of length is such that it will not take a sharp turn when initially deployed through the introducer cannula. For example, the stiffness of the combined aspiration needle assembly 300 may be such that for the first quarter inch of travel beyond the distal end of the introducer cannula 202, the aspiration needle assembly will not bend more than 10 degrees with manual force and it will not penetrate cortical bone. The persistence in length of the aspiration cannula may be such that the maximum angle of deflection for the first 0.5 inch segment of the aspiration cannula that extends beyond the distal end of the introducer cannula is between 0 and 30 degrees. The persistence in length prevents the edge of the distal end of the introducer cannula 202, through which the flexible needle assembly 300 is deployed, from shaving off a portion of the outer surface of the flexible aspiration cannula 302 when the aspiration cannula is being pulled back out of the marrow space.

In one embodiment, the stiffness of the stylet, such as stylet 312 of FIG. 3, varies along the length of the stylet. In addition, the diameter of the stylet 312 may vary along the length of the stylet to vary the stiffness of the stylet. For example, the stylet may have a larger diameter near its distal end as compared to mid section of the proximal end of the stylet. The diameter of the stylet, however, may not be larger than the smallest inner diameter of the aspiration cannula 302.

Figure 12A:
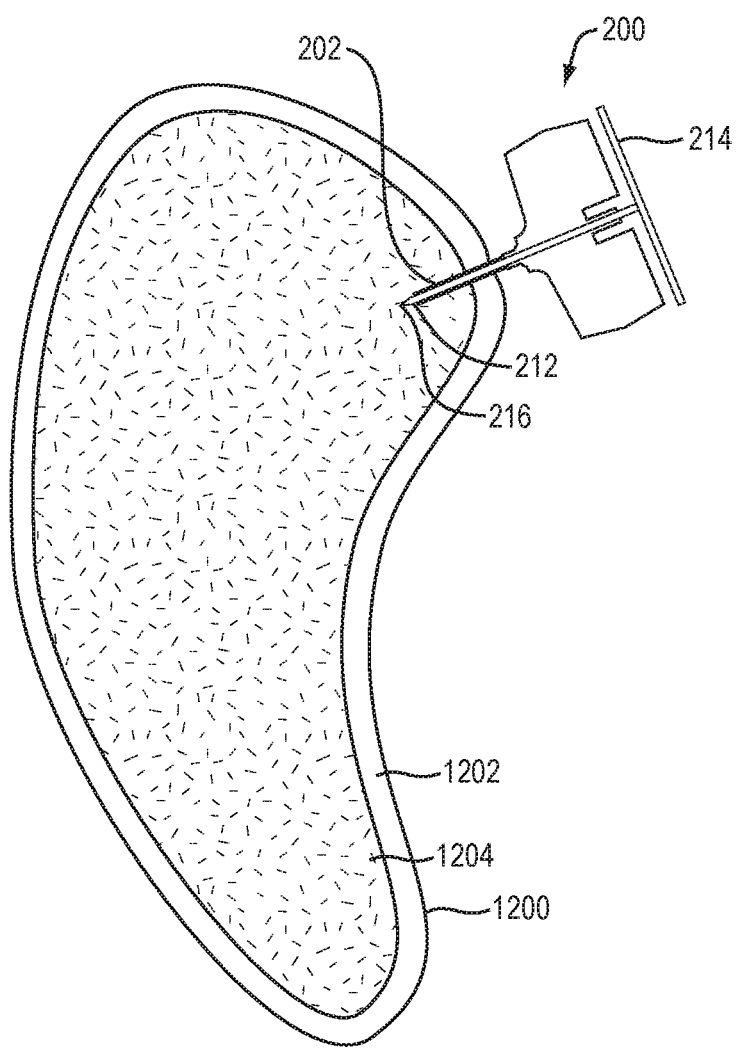
Figure 12B:
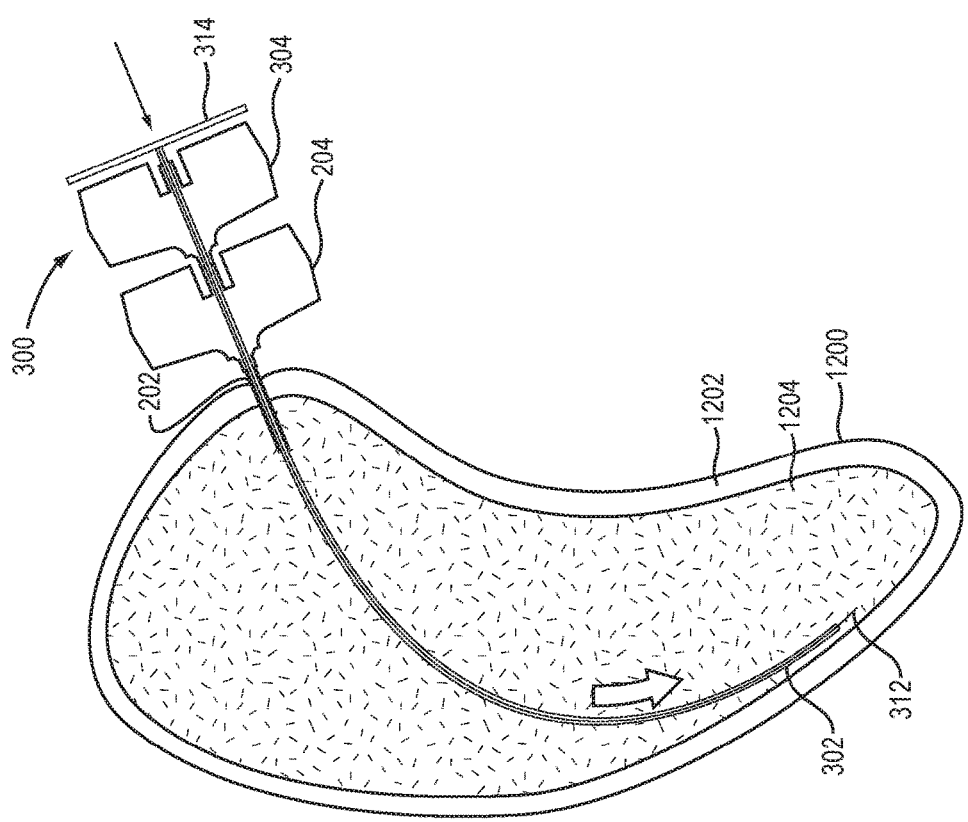

FIG. 12A-C are a series of sequential diagrams illustrating aspiration of bone marrow 1204 from a hip bone 1200 according to an embodiment of the invention. FIG. 12A shows the introducer needle assembly 200, including introducer cannula 202 and trocar 212 with sharp tip 216, penetrating cortical bone 1202 and trabecular bone, including bone marrow, 1204 of hip bone 1200. Access to the hip bone 1200 is from the front. After the introducer needle assembly 200 is in place, the stiff trocar 212 and handle 214 are removed leaving the introducer cannula 202 in place.

FIG. 12B shows insertion of the flexible aspiration needle assembly 300 through the introducer cannula 202 into trabecular bone and bone marrow 1204 of hip bone 1200. The flexible aspiration needle assembly 300 is stiff enough to pass through trabecular bone and marrow 1204, but is not stiff enough to penetrate cortical bone 1202. The aspiration needle assembly 300 has a degree of flex to bend in the curved inner marrow space framed by cortical bone 1202. Thus, the user of the flexible aspiration needle assembly 300 can be assured that an improper insertion angle will not result in trauma due to the needle assembly 300 advancing out of the marrow cavity. After the flexible aspiration needle assembly 300 is inserted to the desired location or depth in the hip bone 1200, the flexible stylet 302 and attached stylet handle 314 are removed, for example by manually pulling on the stylet handle 314.

FIG. 12C shows the aspiration of bone marrow through the flexible aspiration cannula 302 into a syringe 106 or other container or source of vacuum connected to the handle 304 of the aspiration cannula. After the stylet 314 is removed, the aspiration cannula 302 forms a channel for aspirating the bone marrow 1204. The syringe 106 is connected to distal end 310 of the aspiration cannula 302. The distal end 310 of the aspiration cannula may include a luer connection. The luer connection may be included in the aspiration handle 304 and may become exposed or accessible upon removal of the flexible stylet 314. The aspiration cannula 302 maybe be retracted or withdrawn from the hip bone 1200 and through the introducer cannula 202 as the bone marrow is aspirated, as indicated by the single arrow in FIG. 12C. Alternatively or in addition, a fluid may be injected from the connected syringe 106 or other container into the marrow space 1204 as the aspiration cannula 302 is withdrawn, as indicated by the double arrow adjacent the plunger of syringe 106.

Embodiments of the invention have been described for use in bone marrow aspiration. However, embodiments of the invention can be used to aspirate as well as deliver medicine, biologics or other therapy in various tissues. The aspiration device features a double needle assembly. The first or introducer needle assembly, such as assembly 200 of FIG. 2, is stiff enough to make an initial penetration of outer tissue to reach certain targeted subcutaneous tissue. The second, flexible needle assembly, such as assembly 300 of FIG. 3, fits coaxially through the cannula of the first needle assembly. As described above with reference to FIGS. 10 and 12, the aspiration needle assembly will have the stiffness to pass through certain less stiff target tissue but will not have the stiffness to penetrate other, stiff tissue surrounding the target tissue. With respect to the aspiration needle assembly 300, it has enough flex and the aspiration cannula is sufficiently lubricious that the stylet 312 can be removed from the cannula 302 even when both are significantly bent.

Besides bone tissue, various other tissues have different stiffness. For example, tendons and ligaments are stiffer than adipose tissue. Clinicians have a need to both deliver and aspirate various fluids. Embodiments of the present invention can be adapted for specific uses. For example the introducer needle assembly 200 can have a stiffness that will penetrate the intra-articular space in a joint. The flexible aspiration needle assembly 300, when deployed through the first needle, can have a stiffness such that it will penetrate synovial fluid but not other tissue, such as a ligament tissue. The longer, flexible aspiration needle assembly 300 will not take a set so that it can be easily retrieved through the introducer cannula. Thus the aspiration needle assembly 300 can be used to gain access to a substantial cross section of underlying tissue to deliver therapy through the hollow aspiration cannula with only one external puncture that is made by the introducer needle assembly 200. Another example could be to use the introducer needle assembly to gain access to the femur and use the aspiration needle assembly to travel up the length of the femur to the femoral head. Medication or cells could be delivered through the cannula of the aspiration needle assembly under the femoral head for example, in the treatment of osteonecrosis.

Many different materials could used to make the aspiration needle assembly 300, including the long stylet 312 and aspiration cannula 302. In the case of marrow aspiration, the aspiration needle assembly needs to be stiff enough to penetrate trabecular bone, including bone marrow, but flexible enough to bend without taking a set, i.e., without kinking or permanently deforming, when it comes into contact with cortical bone. The longer flexible aspiration cannula also needs to be able to bend without taking a set while traveling back along the path created during insertion. If the aspiration cannula collapses, kinks, etc. while being retracted along the path created during insertion, aspiration will not be possible or will be greatly reduced.

The stylet and cannula of the aspiration needle assembly, such as stylet 314 and cannula 302 of FIG. 3, can be made from various materials including plastics, polytetrafluoroethylene (PTFE), polyetheretherketon (PEEK), or metal, including spring steel or shape memory metal. Various prototypes have been made from these different materials. The materials in combination and individually can be selected to have a desired flex and elasticity specific to the particular application. The purpose of the description is not to limit the choice of materials but to give an example of types of material that work. The introducer cannula, such as cannula 202 of FIG. 2, may include any combination of stainless steel, titanium, spring steel, and nickel titanium.

In the case of bone marrow aspiration, the preferred material of construction for the aspiration needle assembly, such as assembly 300 of FIGS. 3 and 12B, are be PEEK for the flexible cannula and spring steel for the flexible stylet. The introducer cannula, such as cannula 202 of FIGS. 2 and 12A, preferably comprises stainless steel, titanium, or nickel titanium. The introducer trocar, such as trocar 212 of FIGS. 2 and 12A, preferably comprises steel.

In accordance with an embodiment of the invention, prototype introducer and aspiration needle assemblies were constructed. A range of bending stiffness values was determined from the maximum and minimum outer diameters (ODs) and inner diameters (IDs) of the tubing/wire used to make the trocar, stylet, and cannulae in the various materials. Results are shown in Table 1. The bending stiffness EI of a beam, such as a stylet or cannula, relates the applied bending moment to the resulting deflection of the beam and is the product of the elastic modulus E of the beam material and the area moment of inertia I of the beam cross-section.

TABLE 1

Bending Stiffness (EI) measurements for prototypes of the trocar, introducer cannula, stylet, and aspiration cannula, where EI is the product of the elastic modulus (E) of the component material and the area moment of inertia (I).

|  | Trocar | Introducer Cannula | Stylet | Aspiration Cannula |
|---|---|---|---|---|
| Material | 304 SS | 304 SS | 304 SS | 381-G Peek |
| E (MPa) | 200000 | 200000 | 200000 | 4300 |
| Max OD (m) | 0.0033655 | 0.0042164 | 0.0017653 | 0.0030734 |
| Min OD (m) | 0.0033401 | 0.0041656 | 0.0017399 | 0.0030226 |
| Max ID (m) | N/A | 0.0034798 | N/A | 0.0019304 |
| Min ID (m) | N/A | 0.0033782 | N/A | 0.0018796 |
| Max I (m^4) | 6.2975E−12 | 9.12137E−12 | 4.76698E−13 | 3.76704E−12 |
| Min I (m^4) | 6.10952E−12 | 7.5826E−12 | 4.49849E−13 | 3.4156E−12 |
| Max EI (N*m^2) | 1.2595E−06 | 1.82427E−06 | 9.53397E−08 | 1.61983E−08 |
| Min EI (N*m^2) | 1.2219E−06 | 1.51652E−06 | 8.99698E−08 | 1.46871E−08 |

Of equal importance to being able to source tissue, such as bone marrow, is the ability to be able to separate and concentrate target cells, such as nucleated cells, from the sourced material. The devices and systems described herein allow a surgeon or operator at a cord blood bank to separate and concentrate the target cells from the tissue. The separation systems generally includes a container defining a cavity adapted to contain a physiological fluid containing cells to be subjected to centrifugation. An insert disposed in the cavity is adapted to move freely in the fluid based on the specific gravity of the insert compared to the specific gravity of the fluid. The insert fits coaxially into the cavity of the container and has one or more through holes forming an open fluid path between opposite ends of the insert such that after centrifugation, cells and fluid that have approximately the same density as the insert are contained in the lumen created by the through hole or holes in the insert.

Figure 13:
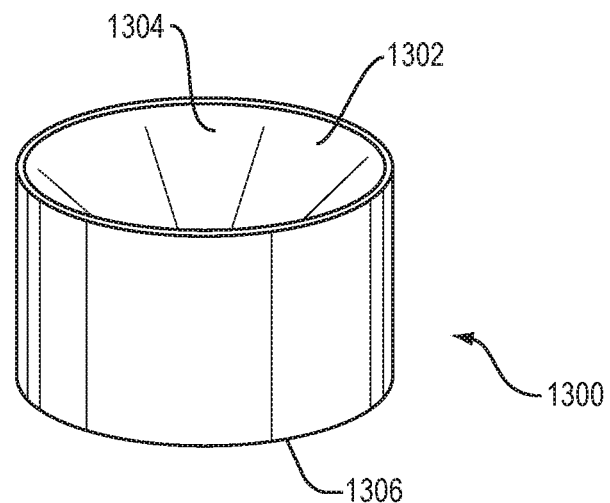
FIG. 13 is a perspective view of an embodiment of an insert for use in a system for separating components of a fluid.

FIG. 13 is a perspective view of an embodiment of an insert 1300 for use in a system for separating components of a fluid. The inner wall 1302 of the insert 1300 forms an upper funnel-shaped portion or cone 1304 and a lower funnel-shaped portion or cone 1306, the wide ends of the funnel or cone located at opposite ends of the insert.

Figure 14:
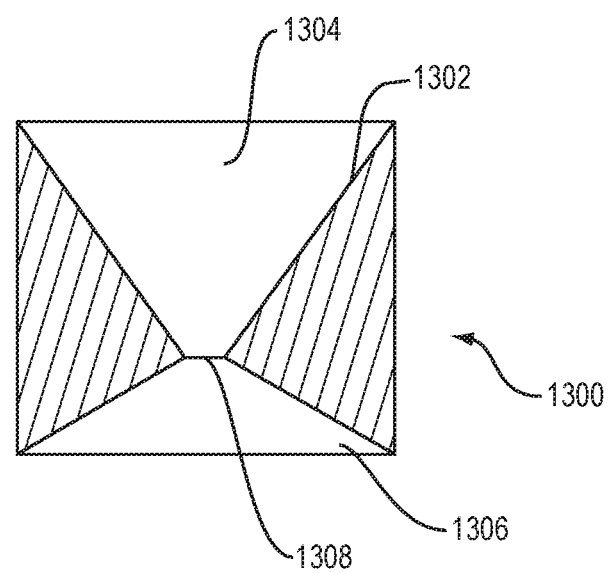
FIG. 14 is a cross-sectional view of the insert of FIG. 13.

FIG. 14 is a cross-sectional view of the insert 1300 of FIG. 13. The insert 1300 includes a through hole 1308. The constricted portions of two funnels or cones 1304 and 1306 are connected in the center at the through hole 1308, creating a fluid path through the insert 1300. The funnel-shaped upper portion need not be conical and need not be symmetric. The hole may be centered in the insert or may be offset.

Figure 15:
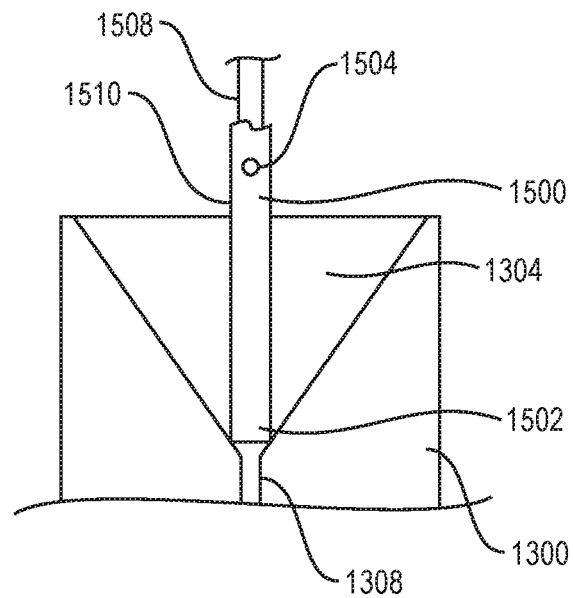
FIG. 15 is a side view of another embodiment of an insert illustrating a cannula with a solid tip closing off the through hole of the insert, the cannula having a side port located above the insert.

FIG. 15 is a side view of another embodiment of an insert 1300 illustrating a cannula assembly 1500 has a solid or closed tip 1302 closing off the through hole 1308 of the insert. The cannula assembly 1500 includes upper side ports 1504 located above the wide end of the upper funnel-shaped portion 1304 of insert 1300. Cannula assembly 1500 has a solid tip 1502 that is lodged into the center constricted portion of the funnel 1304 and may form a seal with insert 1300. When a seal is formed and the insert is disposed in a container or vessel containing a physiological fluid, any fluid or fluid components above the seal are separated from fluid or fluid components below the seal. The cannula assembly 1500 may include an inner cannula within an outer cannula and may include upper side ports 1504 and lower side ports 1506 (FIG. 16) At the orientation depicted in FIG. 15, the top side ports 1504 line up forming a first channel for fluid communication between the inside of the cannula assembly and the outside, but the bottom ports 1506 (FIG. 16) are not lined up and do not form a channel for fluid communication. Consequently, when the operator evacuates fluid through the cannula in this orientation, fluid from the open ports 1504 and above will be evacuated from the container while fluid beneath the ports 1504 but above the seal created by the solid tip of the cannula lodged into the insert will not be.

Figure 16:
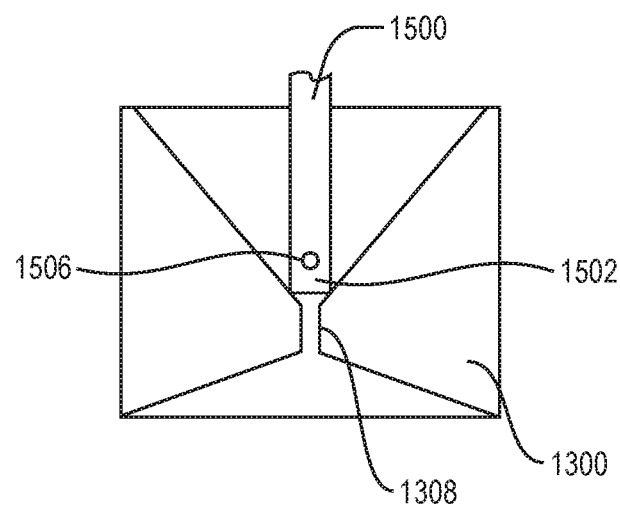
FIG. 16 is a side view of the insert of FIG. 15 illustrating a cannula having solid tip that closes off the through hole of the insert and a side port near the tip.

FIG. 16 is a side view of the insert of FIG. 15 illustrating the cannula assembly 1500 having solid tip that closes the through hole 1308 of the insert 1300 and side ports 1506 near the tip. At the orientation depicted the bottom side ports 1506 line up forming a channel for fluid communication between the inside of the cannula assembly and the outside. The top ports 1504 (FIG. 15) are not lined up and do not form a channel for fluid communication. Consequently, when the operator evacuates fluid through the cannula assembly in this orientation, fluid from the open, bottom side ports 1506 and above will be evacuated from the container. Since the top side ports 1504 (FIG. 15) are closed in this orientation of the cannula assembly, the operator will not pull air until all fluid above the seal is evacuated.

Figure 17:
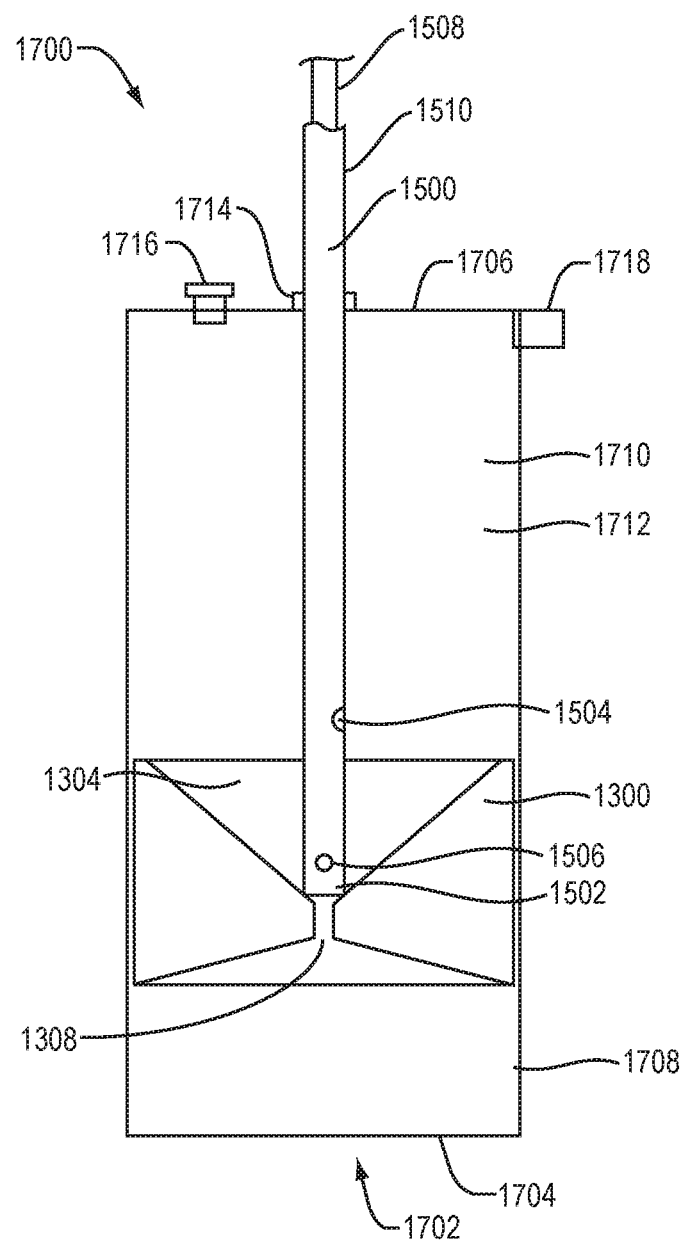
FIG. 17 is a side view of an embodiment of system for separating components of different densities from a fluid containing cells.

FIG. 17 is a side view of a system 1700 for separating components of different densities from a physiological fluid containing cells using a centrifuge. Separation system 1700 includes a container 1702 that has a bottom 1704, a top 1706 disposed opposite the bottom, and a sidewall 1708 extending between the bottom and the top. The container defines a cavity 1710 for receiving the physiological fluid 1712. The system further includes a rigid insert 1300 slidably disposed in the cavity, the insert including a funnel-shaped upper portion 1304 and a hole 1308 therethrough. The insert has a density such that upon centrifugation a selected component of the fluid resides within the upper portion of the insert. Also included is a port 1714 disposed in the top of the container and a cannula assembly 1500 receivable in the port to butt against the insert and withdraw the selected component. The cannula assembly 1500 includes a closed end 1502 to close the hole in the insert and a side port or side ports 1506 to withdraw the selected component. The cannula assembly 1500 and the insert 1300 can form a seal when the closed end of the cannula closes off the through hole 1308 in the insert.

As shown in FIG. 17, the cannula assembly 1500 can include an inner cannula 1508 and an outer cannula 1510, the inner cannula being coaxially disposed with the outer cannula. The cannula assembly can further include a first set of side ports 1506 into the cannulae and a second set of side ports 1504 into the cannulae to open a first channel or a second channel, respectively, through the cannula assembly. Alignment of the of the first set of ports or the second set of ports with relative rotation of the inner or outer cannula opens the first channel or the second channel, respectively. In one embodiment, alignment of the first set of ports causes misalignment of the second set of ports, thereby closing the second channel. Alignment of the second set of ports causes misalignment of the first set of ports, thereby closing the first channel.

At the orientation of the inner and outer cannulae shown in FIG. 17, the top ports 1504 into cannula 1500 line up forming a channel for fluid communication between the inside of the cannula 1500 and the fluid 1712, but the bottom ports 1506 into the cannula assembly 1500 are not lined up and do not form a channel for fluid communication.

The separation system 1700 can include a vent 1716, which may be disposed in the top 1706 of the container 1702, and a fluid port 1718, which may be disposed in or adjacent the top 1706 or the container 1702. Fluid port 1718 may include a luer connection. Vent 1716 and fluid port 1718 may each include a cap to close the vent and the fluid, respectively.

Figure 18:
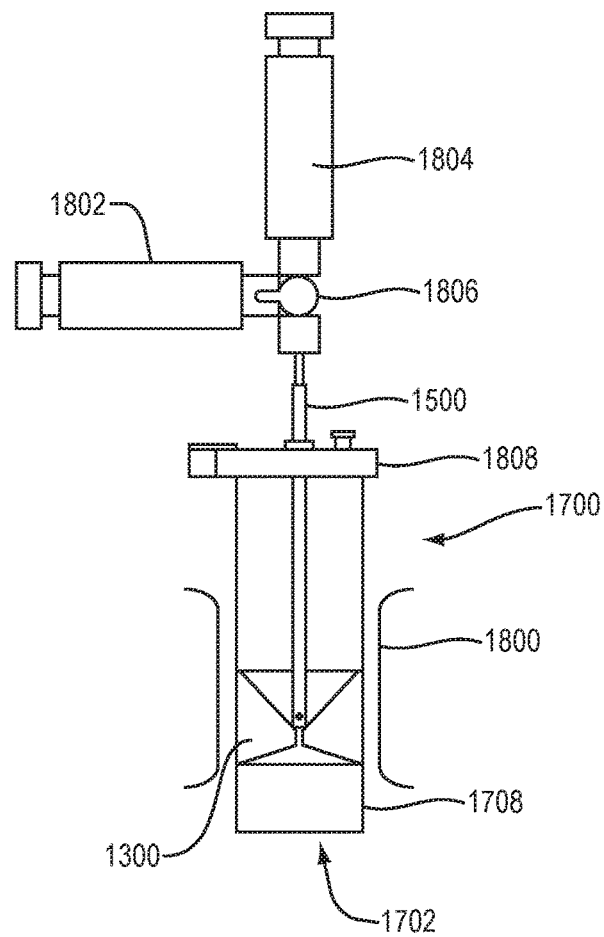
FIG. 18 is a diagram illustrating an embodiment of the separation system including a clamp and syringes connected via a valve.

FIG. 18 is a diagram illustrating an embodiment of the separation system 1700 coupled to a clamp 1800 and two syringes 1802, 1804. In one embodiment, the distance between the outer wall of the insert 1300 and inner surface of sidewall 1708 of the container 1702 is small enough to allow for the insert to be locked in place by applying a clamp 1800 to the outside of the sidewall parallel to where the insert 1300 is located. The pressure of the clamp will flex the sidewall of the container 1300 in at least two points so that the friction created by the contact between the sidewall of the container and the insert will cause the insert to be locked in place.

The syringes 1802 and 1804 are connected to the cannula assembly 1500 via a valve mechanism 1806 to selectively withdraw at least two different components of the fluid from within the container 1702. The top of the container 1702 may include a cap 1808 to close the container. The cap 1808 may be removable.

Figure 19:
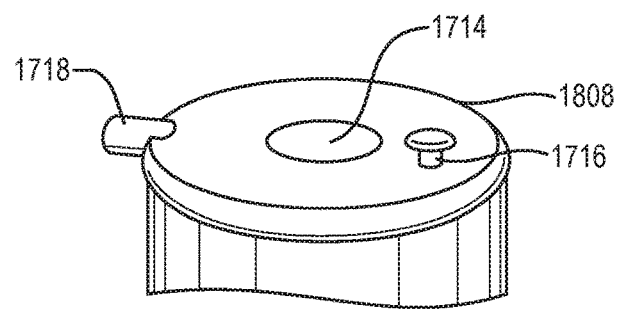
FIG. 19 is a perspective view of an embodiment of the top or cap of the container of the separation system shown in FIG. 18.

FIG. 19 is a perspective view of an embodiment of the cap 1808 of the container of the separation system 1700 shown in FIG. 18. The injection port 1714, the fluid port 1718, and the vent 1716 may be disposed in the cap. The fluid port 1718 may include a luer connection for loading fluid. The injection port 1714 is adapted to receive a cannula, such as cannula assembly 1500, for retrieving fluid through the action of a cannula connected to a syringe or other suction device. The air vent 1716 can prevent a vacuum from being created when fluid is withdrawn from the container 1702.

Figure 20:
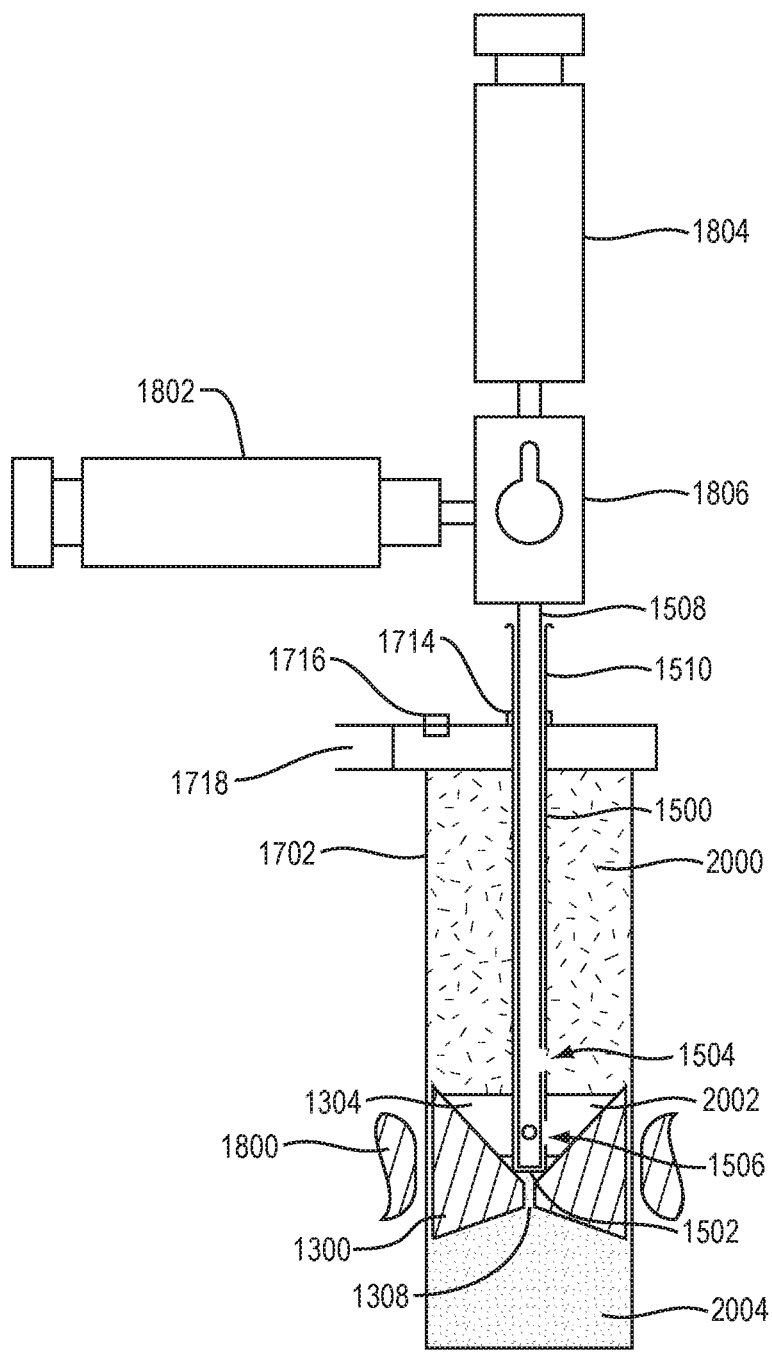
FIG. 20 is a diagram illustrating an embodiment of the separation system showing different components of a fluid after centrifugation.

FIG. 20 is a diagram illustrating an embodiment of the separation system 1700 showing different components of a fluid inside the container 1702 after centrifugation. After centrifugation, the least dense fluid 2000 will be above the insert 1300. The insert can be made of a material of a certain density such that after centrifugation of blood, including blood from marrow, the insert spans the space between the least dense plasma 2000 and the dense red cells 2004, with the intermediate dense material 2002, e.g., nucleated cells, residing in the upper funnel-shaped portion 1304 of the insert.

A cannula assembly 1500 with a solid point or closed end 1502 is inserted through the injection port 1714. Before insertion of the cannula assembly, a clamp 1800 can be applied to sidewall of container 1702 to hold the insert 1300 in place during subsequent fluid extraction. The closed end 1502 of the cannula assembly butts against the insert and closes the through hole 1308. The closed end of the cannula assembly 1500 and the insert can form a seal, thus isolating denser fluid component or components beneath the seal from fluid components above the seal. As described above with reference to FIG. 17, the cannula assembly includes two cannulae or tubes, an inner cannula 1510 and an outer cannula 1508, that fit coaxially into each other.

In one embodiment, the cannula assembly includes a series of at least two parallel side holes or ports in the two cannulae to line up at different predetermined heights above the closed distal end 1502. A first set of side ports 1506 can be located near the closed distal end 1502. A second set of side ports 1504 can be located above the upper funnel-shaped portion 1304 of insert 1300. Fluid above the distal end 1502 of the cannula assembly can be removed in at least two fractions or components based on these two different predetermined heights. Fluid can be removed through the cannula assembly 1500 into connected syringes 1802, 1804 using valve 1806. For example, when the top side ports 1504 are aligned and opened, fluid above the top side ports can be extracted into a first syringe 1802. By rotating the two cannulae with respect to each other, the top side ports in the cannula 1500 are misaligned and sealed off, while the bottom side ports are aligned and opened. As shown in FIG. 20, the side ports may be radially offset by 90 degrees, requiring a relative rotation of 90 degrees to change which ports are aligned. When the bottom side ports 1506 are located just above the seal created by the closed end 1502 of the cannula assembly, substantially all fluid above the seal, but below the top side ports, can be extracted into a second syringe 1804.

FIG. 21 is perspective view of an alternative embodiment of a separation system that includes a container with a movable bottom or plunger. The system 2100 for separating components of different densities from a fluid containing cells using a centrifuge includes a container 2102 having a top 2106, a sidewall 2108 extending from the top, and a movable bottom or plunger 2104 in sealing engagement with the sidewall 2108. The container defines a cavity 2110 for receiving the fluid. The system further includes a rigid insert 1300 slidably disposed in the cavity and defining a lumen through the insert, the lumen including a hole 1308 (FIG. 13) and a funnel-shaped upper portion 1304 in fluid communication with the hole. The insert has a density selected such that upon centrifugation a selected component of the fluid resides within the lumen. The selected component may be buffy coat.

The container 2102 can be a tube that is part of a syringe ("collection syringe"). For example, in this embodiment there can be three openings near the top 2106 of the container, the top being the normally distal end of the collection syringe. One opening that is off center is a fluid port 2118, which can include a standard luer connection. The center opening can be an injection port 2114. The third opening, which is also off center, is an air vent 2106 with a cap.

FIG. 22 is a top view of the separation system of FIG. 21. When the air vent is capped as shown in FIG. 22, the collection syringe container 2102 supports a vacuum. When the air vent is not capped, the collection syringe container 2102 no longer supports a vacuum.

The movable bottom or plunger 2104 of the syringe can have a removable handle (not shown). Alternatively, the collection syringe 2102 can have no handle, just a plunger, and can be loaded through fluid port 2114.

The system 2100 also includes fluid port 2118 disposed adjacent the top of the container for withdrawing a fluid component having a lower density than the selected component, e.g., for withdrawing plasma. The first port is closed by the insert 1300 with upward movement of the insert and the movable bottom 2104. FIG. 23 is a top view of the separation system of FIG. 21 illustrating connection of a first syringe 2300 to a first port, which is the fluid port 2118.

FIG. 24 is a side view of a cannula 2400 connected to a second syringe for insertion into the container 2102 of the separation system 2100 of FIG. 21. The separation system includes the cannula 2400 for withdrawing a selected component, such a buffy coat, from the lumen of the insert 1300.

FIG. 25 is a perspective view of the separation system 2100 of FIG. 21 showing the first syringe 2300 connected to the first or fluid port 2118 and the cannula 2400 connected to a second syringe 2302 inserted into the container 2102 through the second or injection port 2114 disposed in the top 2106 of the container.

Figure 26:
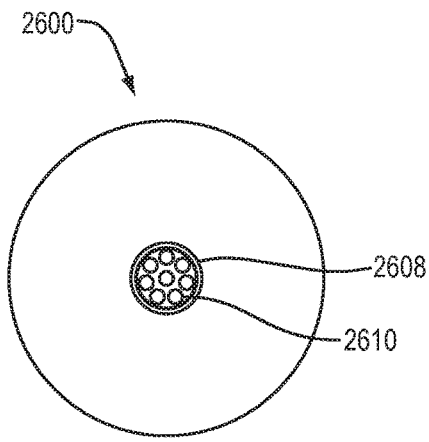
FIG. 26 is a top view of an embodiment of an insert for use in a separation system, the insert having multiple through holes.

FIG. 26 is a top view of an alternative embodiment of an insert having multiple through holes for use in a separation system such as system 2100. The insert 2600 is preferably rigid and includes and inner surface 2602 that defines a lumen through the insert, the lumen including multiple holes, including through holes 2610, and a funnel-shaped upper portion 2604 in fluid communication with the holes. The insert 2600 has a density selected such that upon centrifugation, a selected component of the fluid, i.e., the target cells, resides within the lumen.

Figure 27:
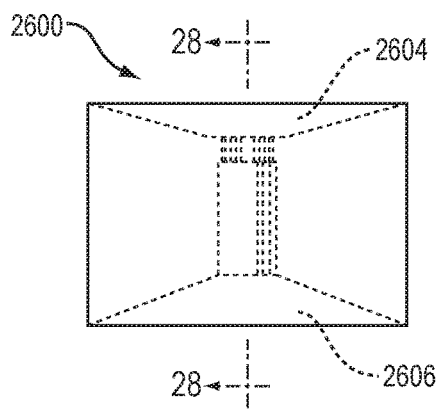
FIG. 27 is a side view of the insert of FIG. 26.
Figure 28:
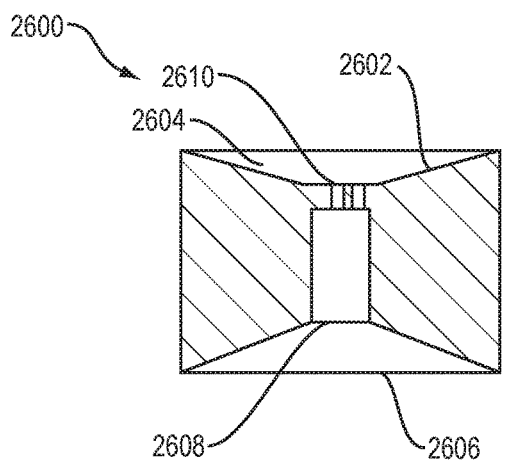
FIG. 28 is a cross-sectional view of the insert along line B-B of FIG. 27.

FIG. 27 is a side view of the insert of FIG. 26. FIG. 28 is a cross-sectional view of the insert 2600 along line B-B of FIG. 27. The top of insert 2700 has a funnel-shaped upper portion 2604 leading to a series of through holes 2610. The holes 2610 are symmetrically arranged in the center of the insert and are connected to a center through hole 2608. The through holes 2610 can be shallow relative to the height of the insert 2700 and the height of the center through hole 2608. Thus, fluid communication to either end of the insert is maintained through the center of the insert. The lower portion 2606 of the insert is shaped like a funnel that is inverted with respect to the top funnel 2604. The funnel-shaped upper portion 2604 and lower portion 2606 need not be conical and need not be symmetric. The hole 2608 and holes 2610 may be centered in the insert or may be offset.

The use of insert 2600 with separation system 2100 is described below. Fluid can be drawn into the collection syringe or container 2102 and then the optional handle can be removed from the plunger 2104. The syringe or container 2102 can be placed in a centrifuge with the plunger facing down and the distal end 2106, including the port 2118, air vent 2116 and injection port 2114 facing up. After centrifugation, the least dense fluid will be above the insert 2600. The insert 2600 can be made of a material of a certain density such that after centrifugation of blood (including blood from marrow) the insert spans the space between the least dense plasma and the densest red cells with the intermediate dense material, nucleated cells, found in the center of the through holes 2608, 2610 of the insert. Nucleated cells will be located in the middle of the through hole or holes of the insert 2600 with plasma above and red cells below. The off center port 2118 is used to first pull plasma fluid from above the insert 2600. The insert is shaped such that when it rises to the top of the syringe and all the plasma fluid above the inset is removed, the solid portion of the outer wall of the insert mates with the top of the syringe or container 2102, sealing the fluid path to the off center port 2118. The vacuum created by extracting the plasma fluid above the insert with a second syringe causes the plunger 2104 and the insert 2600 in the collection syringe to rise in tandem within the collection syringe. The through holes 2608, 2610 of the insert are lined up with the center of the syringe or container 2102. The through holes 2610 on the distal end closest to port 2118 can be sized to be smaller to a certain depth. After a certain depth, the through holes 2118 can become significantly larger or even a single hole 2608. Thus less pressure is needed to pull the less dense material above the insert into the extracting syringe than is needed to pull target cells out of the through holes 2610 in the insert. Consequently, fluid above and below the insert 2600 do not mix with fluid in the through holes 2610 of the insert during the plasma extraction process. Also, since the cells are captured within the through holes 2608, 2610, they do not mix due to different flow rates caused by friction with the inner wall of the tube. This mechanism is described in more detail with reference to FIG. 30 below.

Figure 29A:
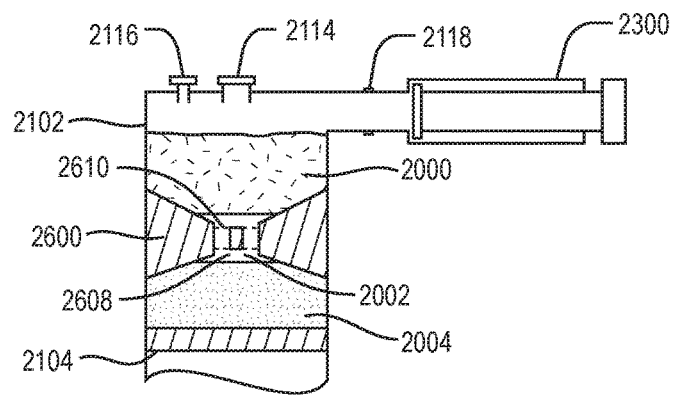
FIGS. 29A-C are a series of sequential diagrams illustrating the extraction of fluid components using an embodiment of the separation system having a movable bottom or plunger.
Figure 29B:
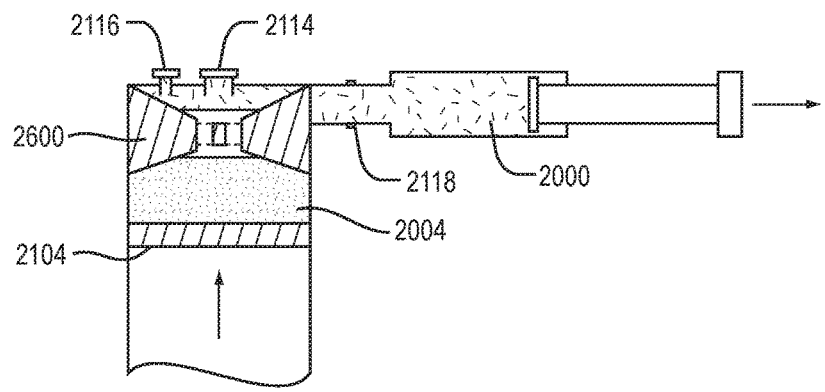
Figure 29C:
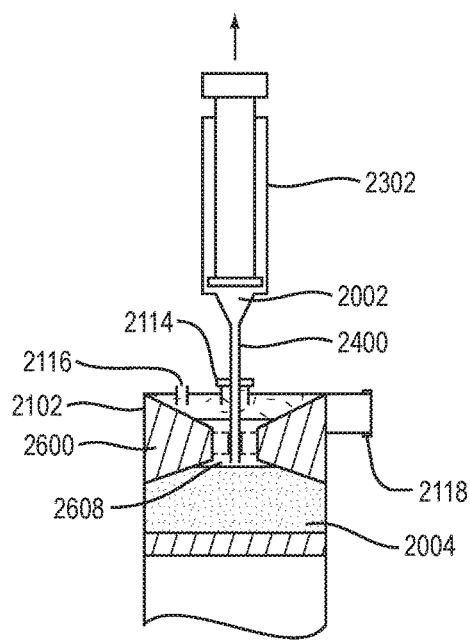

FIGS. 29A-C are a series of sequential diagrams illustrating the extraction of fluid components using an embodiment of the separation system 2100, the system having a movable bottom or plunger. Centrifugation separates the fluid by density into separate components or fractions. FIG. 29A illustrates the position of an insert, such as insert 2600, in relation to three components of a fluid in the separation system 2100 after centrifugation. The components are a low density fraction 2000, such as plasma, a medium density fraction 2002, such as buffy coat or nucleated cells, and a high density fraction 2004, such as blood. In the case of blood when the ports are facing up and the plunger is facing down in the centrifuge, after centrifugation:

a. substantially all plasma will be above the insert (between the insert and luer connection(s)/air vent),
b. the insert itself will span the demarcation line between plasma and red blood cells and thus the through channel of the insert will contain nucleated cells having a density less than red cells but greater than plasma, and
c. red blood cells will be under the insert (between the insert and the movable base).

To retrieve the separated layers or fluid components, the user takes the syringe or container 2102 out of the centrifuge. As shown in FIG. 29B, the user then uncaps the luer connector of port 2118, attaches a plasma extraction syringe 2300, and pulls back on the plunger. The calculated combination of 1) the fluid flow of plasma as it is being evacuated from the collection syringe or container 2102, which can be lateral to the center injection port, 2) the size of the center hole 2608 or holes 2610 in the insert 2600, 3) the relative density of the different fluids inside the container 2102, and 4) the forces required to extract fluid of different densities under these known parameters, results in substantially only plasma moving into the plasma syringe 2300. Because the air vent 2116 is capped, the collection syringe or container 2102 is a vacuum. Thus the movable bottom or plunger 2104 and the insert 2600 rise in the collection syringe or container 2102 as the plasma is extracted. The target cells, such as buffy coat, stay in the through hole or holes 2610 of the insert 2600.

As shown in FIGS. 29B-C, after removal of the plasma 2000, the insert 2600 has risen to the top of the syringe or container 2102 and effectively seals off port 2118 connected to the plasma extraction syringe. At this point the user uncaps the air vent 2116 making the collection syringe or container 2102 no longer under vacuum pressure. A second target cell extraction syringe 2302 with a cannula 2400 attached is then inserted through the center injection port 2114.

Since 1) the insert 2600 always ends up at the top of the collection syringe or container 2102 after removal of the plasma and 2) the height of the insert 2600 is known, then the distance between the top of the injection port 2114 and bottom of the through holes 2610, 2608 of the insert 2600 is always the same after removal of the plasma. The length of the cannula 2400 is such that it reaches just to the bottom of the center through hole 2608 in the insert 2600 after removal of the plasma. Thus, when the user pulls back on the plunger of the target cell extraction syringe 2302, after the air vent 2116 has been uncapped, the target cells residing in the through hole or holes 2610, 2608 are removed.

To retrieve the separated layers, the capped vent 2116 and capped injection port 2114 prevent air from entering the container 2102, whereby the vacuum created by aspirating with the first syringe 2300 through the port 2118 is used to pull the plasma from the container. The plasma is the layer or fluid component closest to the port 2118. During withdrawal of the plasma, the movable bottom or plunger 2104, insert 2600, and fluid between these will have risen to the point where the insert 2600 encounters the top of the container and seals the side port 2118. Next, the air vent 2116 is uncapped, allowing air to fill the volume emptied by aspirating the nucleated cells or buffy coat into the second syringe 2302.

The container 2102 in this example is a syringe but any device that forms a vacuum, has a plunger, with an optional removable handle, one or more luer connections, an air vent that can be capped would suffice.

Figure 30A:
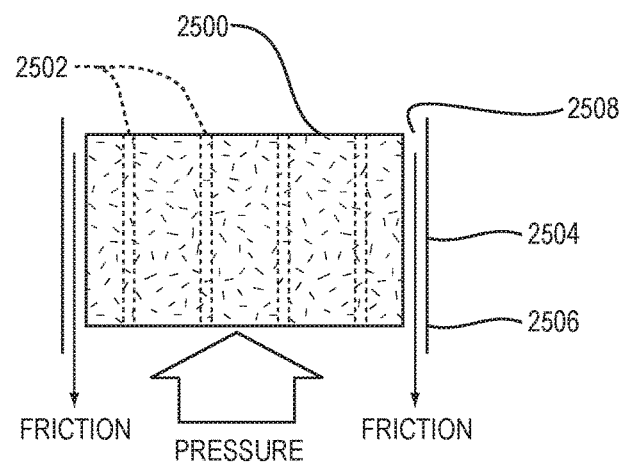
FIGS. 30A-C illustrate the theory of operation of an insert for a separation system.
Figure 30B:
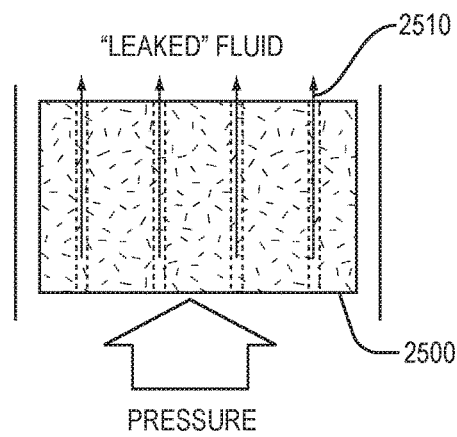
Figure 30C:
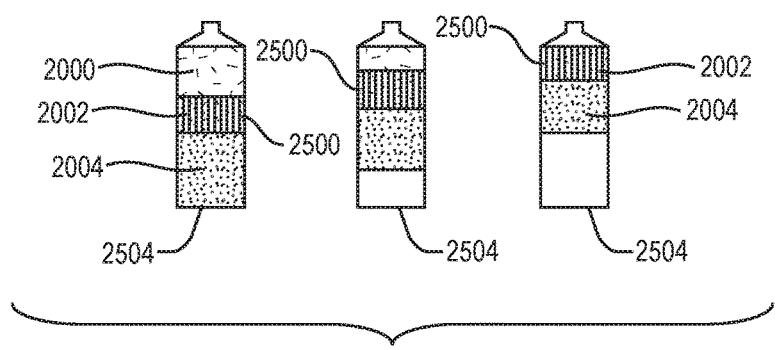

FIGS. 30A-C illustrate the theory of operation of an insert, such as insert 2600, for a separation system, such as system 2100, described herein. FIG. 30A shows rigid insert 2500 having through holes 2502. The insert is slidably disposed in container 2504 having sidewalls 2506. The spacing 2508 between the side walls of insert 2500 and the sidewalls 2506 of container 2504 determines the friction resisting the sliding of the insert, which in turn determines the pressure needed to move the insert. FIG. 30B shows fluid 2510 leaking out of the holes 2502 of insert 2500. The applied pressure pushes the fluid 2510 through the holes or channels 2502. The narrower the holes 2502, the less fluid 2510 moves through them with applied pressure. FIG. 30C shows, from left to right, sequential steps of extraction of plasma from a separation system, such as system 2100. At the far left, after centrifugation, the medium density fraction, e.g., buffy coat, resides in the holes 2510 of insert 2500, the insert being slidably disposed in container 2504. Plasma 2000 resides above the insert and red blood cells 2004 below the insert. The diameter of the channels of holes 2502 is selected so that the buffy coat will not be leaked in to the plasma during extraction of plasma. The result is that the target cells of the buffy coat hardly move with respect to the interior of the through holes 2510, even though the insert 2500 moves upward with extraction of the plasma, as shown in the middle and right of FIG. 30C. This result enables a high-yield separation of target cells.

Figure 31:
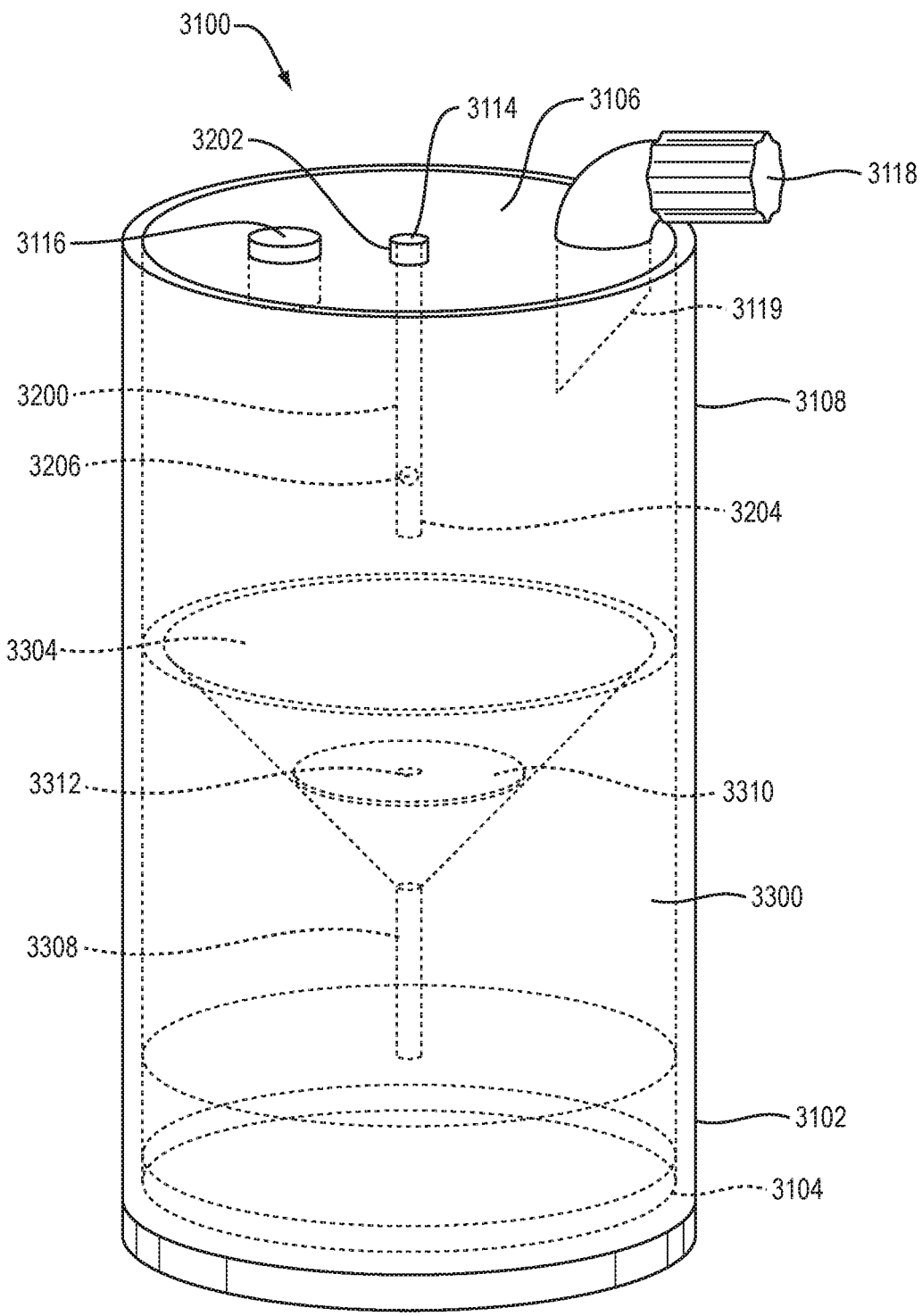
FIG. 31 is a perspective view of an alternative embodiment of the separation system that includes a fixed cannula extending from the top of the container into the container.

FIG. 31 is a perspective view of an alternative embodiment of the separation system having movable bottom or plunger that includes a fixed cannula extending from the top of a container into the container. The separation system 3100 of FIG. 31 operates similar to separation system 2100, but does not requires insertion of a cannula to withdraw a selected component of fluid from a hole or lumen or constricted region of the insert.

The separation system 3100 includes a container 3102 that has a top 3106, a sidewall 3108 extending from the top, and a movable bottom 3104 in sealing engagement with the sidewall. The container defines a cavity for receiving the fluid. The system further includes a rigid insert 3300 slidably disposed in the cavity. The insert 3300 defines a lumen through the insert, the lumen including a hole 3302 and a funnel-shaped upper portion 3304 in fluid communication with the hole. The funnel-shaped upper portion need not be conical and need not be symmetric. The hole may be centered in the insert or may be offset. The insert has a density selected such that upon centrifugation a selected component of the fluid, such as buffy coat, resides within the lumen above the hole 3302. The system also includes a first port 3318 disposed adjacent the top or cap 3106 of the container for withdrawing a fluid component having a lower density than the selected component, such as plasma, the first port being closed by the insert with upward movement of the insert 3300 and movable bottom 3104. The first port may include an angled portion 3119 to mate with the upper-funnel portion 3304 of the rising insert 3300 as plasma is removed.

The system includes a fixed extraction cannula 3200 for withdrawing the selected component from the lumen of the insert. The cannula 3200 includes a proximal end 3202 attached to the top 3106 of the container and a distal end 3204 extending into the container. The cannula includes a side port 3206 to withdraw a selected component, such as buffy coat, from the funnel-shaped upper portion of the insert. The distal end 3204 of the cannula is closed and adapted to mate with the insert 3300 to close the hole 3308 in the insert with upward movement of the insert. The cannula can be molded as part of the top or cap of the container. The cannula connects with port 3114, which can include a luer connector. Also included is an air vent 3116 that can be capped.

The insert 3300 can have a separate washer 3310 with a center hole 3312 to keep fluid components or target cells residing below the washer from moving when plasma is withdrawn from above the washer. The washer 3310 may or may not be attached to the insert 3300. After centrifugation, the target cells, including buffy coat, preferably reside beneath the washer 3310 but above the hole 3308 at the bottom of funnel-shaped portion 3304.

Figure 32:
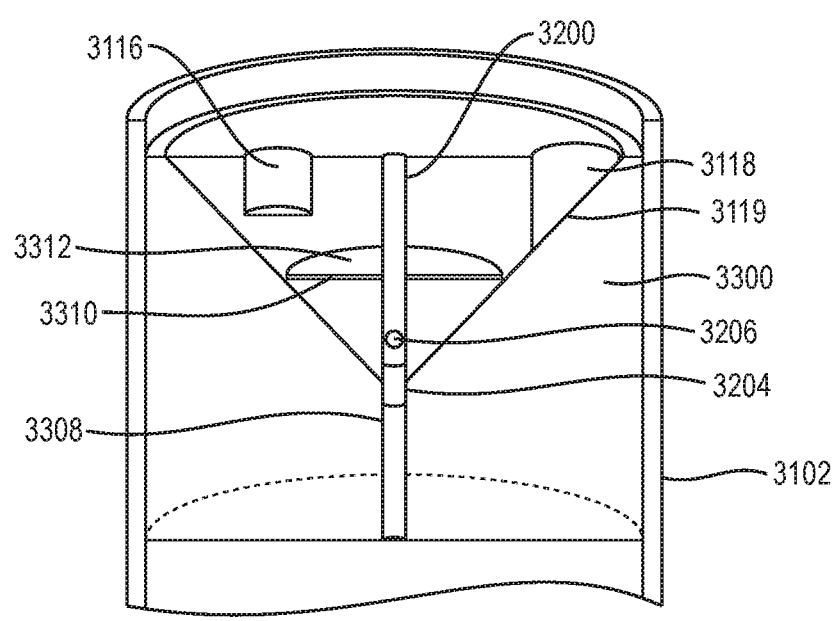
FIG. 32 is an enlarged cross-sectional view the separation system of FIG. 31.

FIG. 32 is an enlarged cross-sectional view the separation system of FIG. 31 illustrating the position of the insert 3300 after removal of the plasma. The angled portion 3319 of the plasma retrieval port 3318 is engaged with the insert 3300, effectively sealing off the port 3318. The extraction cannula 3200 is engaged with the center hole of the washer. The closed end of the cannula is engaged with the bottom of the he upper funnel-shaped portion 3304 of insert 3300, closing off the center hole 3308.

Figure 33:
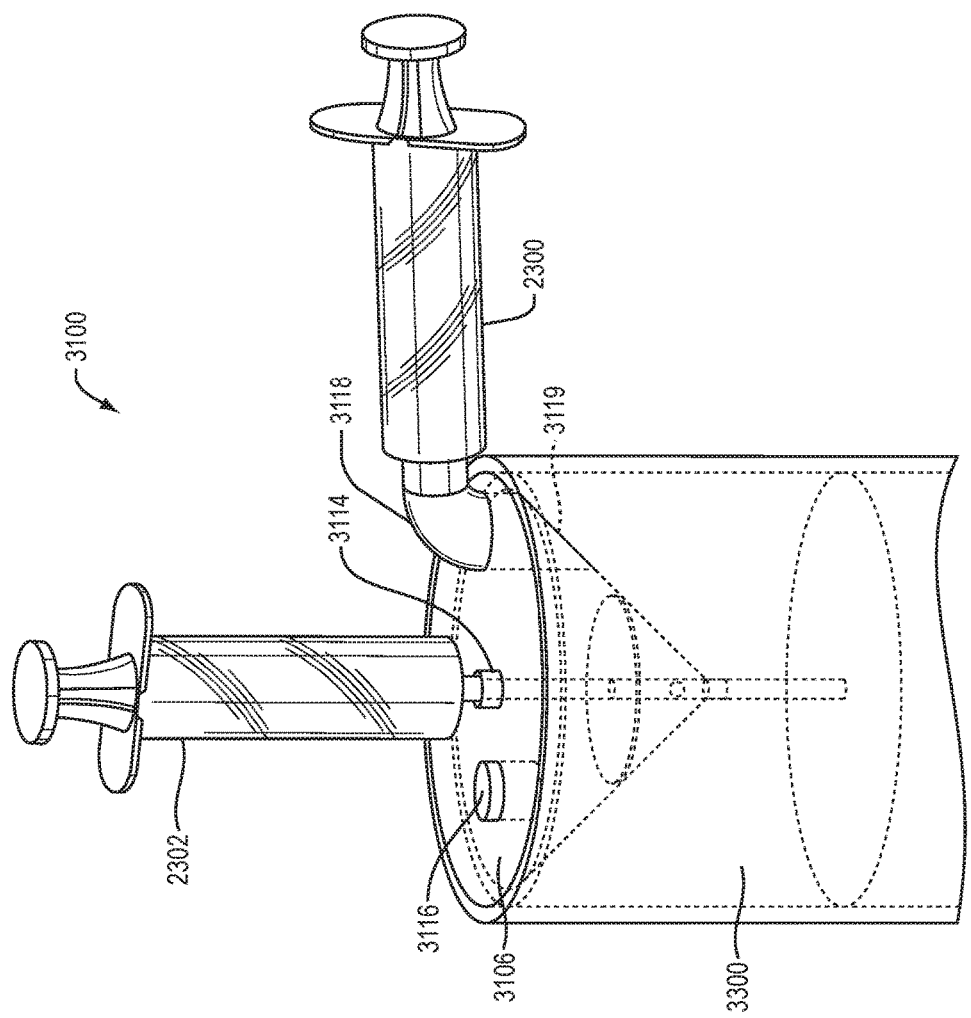
FIG. 33 illustrates attachment of two syringes to the separation system of FIG. 31 for extraction of two fluid components.

FIG. 33 illustrates attachment of two syringes 2300, 2302 to the separation system 3100 of FIG. 31 for extraction of two fluid components. To remove fluid, the user removes the cap covering the plasma port 3118, attaches syringe 2300, and removes plasma until the port is sealed with upward motion of the insert 330. The rising insert will also mate with the extraction cannula 3200 extending from the top or cap 3106 of the container. The user can now remove the cap of center luer connection of port 3114 connected to the cannula 3200, attach syringe 2302, and remove the target cells. The extraction cannula 3200 can be attached to or built into the top or cap 3106 of the container. Alternatively, the cannula 3200 may be removable. As described elsewhere herein, the user could also insert a cannula attached to a syringe through port 3114, which may include an injection port to receive the cannula, and use the inserted cannula to withdraw the target cells.

It should be noted that several different embodiments of a floating insert, such as inserts 1300, could be used with separation system 3100. Various configurations will allow for target cells to reside in a hole or lumen or constricted region of the insert after centrifugation. The target cells can then be accessed and isolated through a cannula, such as cannula 3200, that has a closed end which mates with the floating insert after the removal of plasma through a separate port.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A system for separating components of different densities from a physiological fluid containing cells using a centrifuge, the system comprising:
   a container, having a bottom, a top disposed opposite the bottom, and a sidewall extending between the bottom and the top, the container defining a cavity for receiving the fluid;
   a rigid insert slidably disposed in the cavity, the insert having a density such that upon centrifugation a selected component of the fluid resides within an upper portion of the insert;
   a container port disposed in the top of the container;
   a cannula assembly including a cannula receivable in the container port to extend into the upper portion and withdraw the selected component from the upper portion of the insert through a lower port in the cannula, the cannula including an upper port displaced from a distal end of the cannula to withdraw fluid at a predetermined height above the distal end of the cannula; and
   a clamping mechanism to hold the insert in place after centrifugation, wherein the clamping mechanism is coupled to the container sidewall to press the sidewall inward against the insert.

2. The system of claim 1, wherein the insert has a hole therethrough, and wherein the distal end of the cannula is a closed end to close the hole in the insert.

3. The system of claim 2, wherein the cannula assembly includes an inner cannula coaxially disposed within an outer cannula, and wherein the lower port is formed by a first set of side ports into the cannulae to open a first channel through the cannula assembly for withdrawing the selected component from the upper portion of the insert with alignment of the first set of ports with relative rotation of the inner and outer cannulae.

4. The system of claim 3, wherein the upper port is formed by a second set of side ports into the cannulae to open a second channel through the cannula assembly for withdrawing a component other than the selected component with alignment of the second set of ports with relative rotation of the inner and outer cannulae.

5. The system of claim 4, wherein alignment of the first set of ports causes misalignment of the second set of ports, thereby closing the second channel, and alignment of the second set of ports causes misalignment of the first set of ports, thereby closing the first channel.

6. The system of claim 4, wherein the selected component is buffy coat and the component other than the selected component is blood plasma.

7. The system of claim 1, wherein volume contained in the upper portion is between 5% and 20% of the volume of the container cavity.

* * * * *